United States Patent [19]
Li et al.

[11] Patent Number: 6,114,158
[45] Date of Patent: Sep. 5, 2000

[54] ORPINOMYCES CELLULASE CELF PROTEIN AND CODING SEQUENCES

[75] Inventors: Xin-Liang Li; Huizhong Chen; Lars G. Ljungdahl, all of Athens, Ga.

[73] Assignee: University of Georgia Research Foundation, Inc., Athens, Ga.

[21] Appl. No.: 09/118,319

[22] Filed: Jul. 17, 1998

[51] Int. Cl.$^7$ .............................. C12N 9/42; C12N 15/56
[52] U.S. Cl. ...................... 435/209; 435/252.3; 536/23.2
[58] Field of Search .................................. 435/209, 252.3, 435/252.33; 536/23.2

[56] References Cited

FOREIGN PATENT DOCUMENTS

WO 98/14597  9/1998  WIPO.

OTHER PUBLICATIONS

Béguin, P. (1983) "Detection of Cellulase Activity in Polyacrylamide Gels Using Congo Red–Stained Agar Replicas" *Analytical Biochem.* 131::333–336.

Black et al. (1994) "Xylanase B from *Neocallimastix patriciarum* contains a non–catalytic 455–residue linker sequence comprised of 57 repeats of an octapeptide" *Biochem. J.* 299:381–387.

Borneman et al. (1989) "Fermentation Products and Plant Cell Wall–Degrading Enzymes Produced by Monocentric and Polycentric Anaerobic Ruminal Fungi" *Applied and Environ. Microbiol.* 55:1066–1073.

Chen et al. (1998) "Two genes of the anaerobic fungus Orpinomyces sp. strain PC–2 encoding cellulases with endoglucanase activities may have arisen by gene duplication" *FEMS Microbiol. Letts.* 159:63–68.

Chen et al. (1997) "Sequencing of a 1,3–1,4–βD–Glucanase (Lichenase) from the Anaerobic Fungus Orpinomyces Strain PC–2: Properties of the Enzyme Expressed in *Escherichia Coli* and Evidence that the Gene Has a Bacterial Origin" *J. Bacteriol.* 179:6028–6034.

Chen et al. (1995) "A cyclophilin from the polycentric anaerobic rumen fungus Orpinomyces sp. strain PC–2 is highly homologeous to vertebrate cyclophilin B" *Proc. Natl. Acad. Sci.* USA 92:2587–2591.

Choi, S.—K. And Ljungdahl, L.G. (1996) "Structural Role of Calcium for the Organization of the Cellulosome of *Clostridium thermocellum*" *Biochemistry* 35:4906–4910.

Dalrymple et al. (1997) "Three *Neocallimastix patriciarum* esterases associated with the degradation of complex polysaccharides are members of a new family of hydrolases" *Microbiology* 143:2605–2614.

Denman et al. (1996) "Characterization of a *Neocallimastix patriciarum* Cellulase CDNA (celA) Homologous to *Trichoderma reesei* Cellobiohydrolase II" *Appl. Environ. Microbiol.* 62:1889–1896.

Dijkerman et al. (1996) "Adsorption Characteristics of Cellulolytic Enzymes from the Anaerobic Fungus Piromyces Sp. Strain E2 on Microcrystalline Cellulose" *Appl. Environ. Microbiol.* 62:20–25.

Durand et al. (1996) "Molecular characterization of xyn3, a member of the endoxylanase multigene family of the rumen anaerobic fungus *Neocallimastix frontalis*" *Curr. Genet.* 30:531–540.

Fanutti et al. (1995) "The Conserved Noncatalytic 40–Residue Sequence in Cellulases and Hemicellulases from Anaerobic Fungi Functions as a Protein Docking Domain" *J. Biol. Chem.* 270:29314–29322.

Filho (1996) "Purification and characterization of a β–glucosidase from solid–state cultures of *Humicola grisea* var. thermoidea" *Can. J. Microbiol.* 42:1–5.

GenBank Accession No. U97153, released in Apr. 1998.

GenBank Accession No. U97154, Submitted Apr. 11, 1997.

GenBank Accession No. AF031934, Submitted Oct. 29, 1997.

Gilbert et al. (1992) "Homologous catalytic domains in a rumen fungal xylanase: evidence for gene duplication and prokaryotic origin" *Mol. Microbiol.* 6:2065–2072.

Gilkes et al. (1991) "Domains in Microbial β–1,4–Glycanases: Sequence Conservatin, Function, and Enzyme Families" *Microbiol. Rev.* 55:303–315.

Harjunpää et al. (1996) "Cello–oligosaccharide hydrolysis by cellobiohydrolase II from *Trichoderma reesei*" *Eur. J. Biochem* 240:584–591.

Henrissat, B. and Bairoch, A. (1993) "New families in the classification of glycosyl hydrolases based on amino acid sequence similarities" *Biochem. J.* 293:781–788.

Hoffrén et al. (1995) "Molecular dynamics simulation of fungal cellulose–binding domains: differences in molecular rigidity but a preserved cellulose binding surface" *Protein Eng.* 8:443–450.

(List continued on next page.)

Primary Examiner—Charles L. Patterson, Jr.
Attorney, Agent, or Firm—Greenlee, Winner and Sullivan, P.C.

[57] ABSTRACT

A cDNA (1,520 bp), designated celF, consisting of an open reading frame (ORF) encoding a polypeptide (CelF) of 432 amino acids was isolated from a cDNA library of the anaerobic rumen fungus Orpinomyces PC-2 constructed in *Escherichia coli*. Analysis of the deduced amino acid sequence showed that starting from the N-terminus, CelF consists of a signal peptide, a cellulose binding domain (CBD) followed by an extremely Asn-rich linker region which separate the CBD and the catalytic domains. The latter is located at the C-terminus. The catalytic domain of CelF is highly homologous to CelA and CelC of Orpinomyces PC-2, to CelA of *Neocallimastix patriciarum* and also to cellobiohydrolase IIs (CBHIIs) from aerobic fungi. However, Like CelA of *Neocallimastix patriciarum*, CelF does not have the noncatalytic repeated peptide domain (NCRPD) found in CelA and CelC from the same organism. The recombinant protein CelF hydrolyzes celloligosaccharides in the pattern of CBHII, yielding only cellobiose as product with cellotetraose as the substrate. The genomic celF is interrupted by a 111 bp intron, located within the region coding for the CBD. The intron of the celF has features in common with genes from aerobic filamentous fungi.

20 Claims, 4 Drawing Sheets

OTHER PUBLICATIONS

Koivula et al. (1996) "The active site of *Trichoderma reesei* cellobiohydrolase II: the role of tyrosine 169" *Protein Eng.* 9:691–699.

Li et al. (1997) "Monocentric and Polycentric Anaerobic Fungi Produce Structurally Related Cellulases and Xylanases" *Appl. Environ. Microbiol.* 63:628–635.

Li et al. (1997) "Two Cellulases, CelA and CelC, from the Polycentric Anaerobic Fungus Orpinomyces Strain Pc–2 Contain N–Terminal Docking Domains for a Cellulase–Hemicellulase Complex" *Appl. Environ. Microbiol.* 63:4721–4728.

Liu et al. (1997) "An endoglucanase from the anaerobic fungus *Orpinomyces joyonii*: characterization of the gene and its product" *Can. J. Microbiol.* 43:477–485.

Millward–Sadler et al. (1996) "Evidence that the Piromyces gene family encoding endo–1,4–mannanases arose through gene duplication" FEMS *Microbiol. Letts.* 141:183–188.

Pages et al. (1997) "Species–Specificity of the Cohesin–Dockerin Interaction Between *Clostridium thermocellum* and *Clostridium cellulolyticum*: Prediction of Specificity Determinants of the Do kerin Domain" *Proteins* 29:517–527.

Rouvinen et al. (1990) "Three–Dimensional Structure of Cellobiohydrolase II from *Trichoderma reesei*" *Science* 249:380–386.

Sheppard et al. (1994) "The use of conserved cellulase family–specific sequences to clone cellulase homologue cDNAs from *Fusarium oxysporum* "*Gene* 150:163–167.

Teeri et al. (1987) "Homologous domains in *Trichoderma reesei* cellulolytic enzymes: gene sequence and expression of cellobiohydrolase II" *Gene* 51:;43–52.

Van Tilbeurgh et al. (1984) "Separation of endo– and exo–type cellulases using a new affinity chromatography method" *FEBS Letts.* 1699:215–218.

Wilson, C.A., and Wood, T.M. (1992) "The anaerobic fungus *Neocallimastix frontalis*: isolatiion and properties of a cellulosome–type enzyme fraction with the capacity to solubilize hydrogen–bond–ordered cellulose" *Appl. Microbiol. Biotechnol.* 37:125–129.

Zhou et al. (1994) "Intronless celB from the anaerobic fungus *Neocallimastix patriciarum* encodes a modular family A endoglucanase" *Biochem. J.* 297:359–364.

```
Celf_Orpin     1   ...........MKILLFASILSFGLVNFANAA.CGGAYAQCGGENFY......GEKCCVSGYKCVYMNQWYSQCQPGASSSN
Cela_Neoca     1   ...........MKNLLASVLSLGLAGLANAA.CGGAWAQCGGENFH......GDKCCVSGHTCVSINQWYSQCQPGGAPSN
Cela_Orpin     1   .............MKFSTVLATLFATGALASECHWQYPCCKDCTVYTDTEGKWGVLNNDWCMIDNRRCSSNNNCSSSI
Celc_Orpin     1   .............MKFSALISTLFAAGAMASRCHPSYPCCNGCNVEYTDTEGNWGVENFDWCFIDESRC....NPGYCKF
Cbhii_Tri      1   MIVGILTTLATLATLAASVPLEERQACS..SVWGQCGGQNW......SGPTCCASGSTCVYSNDYYSQCLPGAASSS
Cbhii_Fusar    1   ..MAYKLILAAFAATALAAPVEERQSCSNGVWAQCGGQNW......SGTPCCTSGNKCVKLNDFYSQCQPGSAEPS Celf_Orpin    65   PP......SNNASNNNNNNDNNNNNNN.NNNNNNNNNNNNSGSGSTQ.........................NFFTNQ
Cela_Neoca    65   NA....SNNNNNNNNNNNNNNNNNNNHNNNNNNNNNNNGGSGSTK..........................NFFDNQ
Cela_Orpin    68   TSQGYPCCSNNNCKVEYTDNDGKWGVENNNWCGISNSCGGGQQQQPTQPTQPQQPT.....QPSSDNFFENE
Celc_Orpin    64   EALGYSCC...KGCEVVYSDEDGNWGVENQQWCGIRDNCTPNVPATSARTTTRTTTTTTVNSLPTSDNFFENE
Cbhii_Tri     70   SSTRAASTTSRVS...............................PTTSRSSSATPPPGSTTRVPPVGSGTATYSGNPFVGVT
Cbhii_Fusar   69   STAAGPSTT.........................ATKTTATGGSSTTAGGSVTSAPPAASDNPYAGVD Celf_Orpin   112   IYANPKFIEEV.NSSIPKLSWDLQQKAQKVKDVPTAVWLA........WEGAPGEVEQHLKAAGSKTVVFILYMIP
Cela_Neoca   113   IYANPKFIEEV.NSSIPRLSYDLQQKAQKVKNVPTAVWLA........WDGATGEVAQHLKAAGSKTVVFIMYMIP
Cela_Orpin   138   IYSNYKFQGEV.DISIKKLNGDLKAKAEKVKYVPTAVWLA........WDGAPQEVPRYLQEAGNKTVVFVLYMIP
Celc_Orpin   137   LYSNYKFQGEV.DQSIQRLSGSLQEKAKKVKYVPTAAWLA........WSGATNEVARYLNEAGSKTVVFVLYMIP
Cbhii_Tri    122   PWANAYYASEVSSLAIPSLTGAMATAAAAVAKVPSFMWLDTLDKTPLMEQTLADIRTANKNGGNYAGQFVVYDLP
Cbhii_Fusar  113   LWANNYYRSEVMNLAVPKLSGAKATAAAKVADVPSFQWMDTYDHISLMEDTLADIRKANKAGGKYAGQFVVYDLP Celf_Orpin   179   TRDCNSNASAG....GAGSLNTYKGYVDNISRTIRSYPNSKVVMVLEPDTLGNLVTG.NSANCQNVRQLHKNALS
Cela_Neoca   180   TRDCNANASAG....GAGNLNTYKGYVDNIARTIRSYPNSKVVMILEPDTLGNLVTA.NSANCQNVRNLHKNALS
Cela_Orpin   205   TRDCGANASAG....GSATIDKYKGYINNIYNTSNQYKNSKIVMILEPDTIGNLVTN.NNDNCRNVRNMHKQALS
Celc_Orpin   204   TRDCNAGGSNG....GADNLSTYQGYVNSIYNTINQYPNSRIVMIIEPDTIGNLVTA.NNANCRNVHDMHKQALS
Cbhii_Tri    197   DRDCAALASNGEYSIADGGVAKYKNYIDTIRQIVVEYSDIRTLLVIEPDSLANLVTNLGTPKCANAQSAYLECIN
Cbhii_Fusar  188   NRDCAAAASNGEYSLDKDGANKYKAYIAKIKGILQNYSDTKVILVIEPDSLANLVTNLNVDKCAKAESAYKELTV
```

FIG. 1A

```
Celf_Orpin    249  YAVNVYGAMNNVSVYLDAAHGKWLGGVT..DKVAAVVKEILNNAPNGK.IRGLSTNVSNY...............Q
Cela_Neoca    250  YGVNVFGSMSNVSVYLDAAHGAWLGSST..DKVASVVKEILNNAPNGK.IRGLSTNISNY...............Q
Cela_Orpin    275  YAISKFGTQSHVKVYLDAAHGAWLNQYA..DQTANVIKEILNNAGSGK.LRGISTNVSNY...............Q
Celc_Orpin    274  YAISKFGTQKNVRVYLDAAHGGWLNSSA..DRTAEVIAEILRNAGNGK.IRGISTNVSNY...............Q
Cbhii_Tri     272  YAVTQLN.LPNVAMYLDAGHAGWLGWPANQDPAAQLFANVYKNASSPRALRGLATNVANYNGWNITSPPSYTQGN
Cbhii_Fusar   263  YAIKELN.LPNVSMYLDAGHGGWLGWPANIGPAAKLYAQIYKDAGKPSRVRGLVTNVSNYNGWKLSTKPDYTESN Celf_Orpin    307  PIASEYSYHQKLASSLSAVGIPNMHFIVDTGRNGVDVSAAFNTSETWCNFVGTGFGERPRGNPNSG.MPLLDAYM
Cela_Neoca    308  SISSEYQYHQKLASALAAVGVPNMHFIVDTGRNGVT.IN....SGTWCNLVGTGLGERPRGNPNAG.MPLLDAYM
Cela_Orpin    333  SIESEYKYHQNLNRALESKGVRGLKFIVDTSRNGANVEGAFNASGTWCNFKGAGLGQRPKGNPNPGSMPLLDAYM
Celc_Orpin    332  PVYSEYQYHQNLNRALESRGVRGMKFIVDTSRNGRNP.....SSATWCNLKGAGLGARPQANP.DPN.MPLLDAYV
Cbhii_Tri     346  AVYNEKLYIHAIGPLLANHGWSNAFFITDQGRSGKQPTGQ.QQWGDWCNVIGTGFGIRPSANTGDS...LLDSFV
Cbhii_Fusar   337  PNYDEQRYINAFAPLLAQEGWSNVKFIVDQGRSGKQPTGQ.KAQGDWCNAKGTGFGLRPSTNTGDA...LADAFV Celf_Orpin    381  WLKTPRESDGSSSGSRA..DPVCSRSDSLRGAPDAGQWFHDYFVQLLRNARPGF*
Cela_Neoca    377  WLKTPGESDGSSSSGSRA..DPNCSSNDSLRGAPDAGQWFHDYFAQLVRNARPSF.
Cela_Orpin    408  WIKTPGEADGSSQGSRA..DPVCARGDSLQGAPDAGSWFHEYFTMLIQNANPPF.
Celc_Orpin    401  WIKTPGESDS...ASSA..DPVCRNSDSLQGAPAAGSWFHDYFVMLLENANPPF
Cbhii_Tri     417  WVKPGGECDGTSDSSAPRFDSHCALPDALQPAPQAGAWFQAYFVQLLTNANPSFL
Cbhii_Fusar   408  WVKPGGESDGTSDTSAARYDYHCGLDDALKPAPEAGTWFQAYFEQLLDNANPSFL
```

FIG. 1B

SEQUENCE LISTING

<160> NUMBER OF SEQ ID NOS: 9

<210> SEQ ID NO 1
<211> LENGTH: 1631
<212> TYPE: DNA
<213> ORGANISM: Orpinomyces sp. PC-2
<220> FEATURE:
<221> NAME/KEY: intron
<222> LOCATION: (187)..(297)

<400> SEQUENCE: 1

```
aaaaattaaa ttttgtaata ttttttttatt tgatataaaa aaaatattag taaattttt     60 ataaaccttt ttctaattat ttaaaaaaag cacaatgaaa attttacttt ttgccagtat    120
tcttagtttt ggtcttgtaa attttgctaa cgctgcttgt ggtggtgctt atgctcaatg    180
tggagggtat ggatatttta tttttataat ttaggaaata aatacttta aataatttaa    240
```

-continued

```
tttaagtatt gattatttta aattattata ttacttataa caaattaaga tatatagtga    300 aaactttac ggtgaaaaat gttgtgtttc tggttacaaa tgtgtttata tgaatcaatg    360
gtattctcaa tgtcaaccag gtgcttcatc atcaaatcca ccttctaata atgcttctaa   420
caataataac aatgataaca acaacaacaa caacaataat aataataata ataataataa   480
taataataat aataataact ctggtagtgg aagtactcaa aacttcttca ctaatcaaat   540
ttatgctaat ccaaaattca ttgaagaagt caattcttct attccaaaat taagttggga   600
cttacaacaa aaggctcaaa aggttaagga tgttccaact gctgtttggt tagcttggga   660
aggtgctcca ggtgaagttg aacaacatct taaggctgct ggttctaaaa ctgttgtatt   720
tattctttac atgattccaa ctcgtgattg taatagtaat gcttctgctg gtggtgccgg   780
tagtcttaac acttacaagg gttatgttga caacatttct agaactattc gtagttatcc   840
aaactctaag gttgttatgg ttcttgaacc agatactctt ggtaatcttg ttactggtaa   900
cagtgctaac tgtcaaaacg tccgtcaatt acacaagaac gctttatcct atgctgttaa   960
tgtttacggt gctatgaata atgttagtgt ttaccttgat gctgcccatg gtaaatggtt   1020
aggtggtgtt actgataagg ttgctgctgt tgttaaggaa atcttaaaca atgctccaaa   1080
tggtaaaatt cgtggtttaa gtactaacgt ttctaactac caaccaattg cttctgaata   1140
ctcctaccac caaaagcttg cttcctctct ttctgctgtt ggtattccaa acatgcactt   1200
tattgttgat actggccgta atggtgttga tgttagtgct gctttcaata catctgaaac   1260
ttggtgtaac tttgtaggta ctggttttgg tgaacgtcca agaggtaatc caaactcagg   1320
tatgccatta ttagatgctt acatgtggct taagactcca cgagaatctg atggttcttc   1380
ctctggtagt agagctgatc cagtttgttc tcgttctgat tctcttagag gtgcaccaga   1440
cgcaggtcaa tggttccacg attatttcgt tcaattatta agaaatgcta gaccaggatt   1500
ctaagttaat taagaagaaa aaaaagatg ataaaaaaat ttcagtatta attattcttt   1560
ttactattac taattaaatg aataatagat aaaatatata ctatatatca tttattgatg   1620
atataaagtt t                                                        1631
```

<210> SEQ ID NO 2
<211> LENGTH: 432
<212> TYPE: PRT
<213> ORGANISM: Orpinomyces sp. PC-2
<220> FEATURE:
<223> OTHER INFORMATION: Description of Artificial Sequence:oligonucleotide

<400> SEQUENCE: 2

```
Met Lys Ile Leu Leu Phe Ala Ser Ile Leu Ser Phe Gly Leu Val Asn
  1               5                  10                  15

Phe Ala Asn Ala Ala Cys Gly Gly Ala Tyr Ala Gln Cys Gly Gly Glu
                 20                  25                  30

Asn Phe Tyr Gly Glu Lys Cys Cys Val Ser Gly Tyr Lys Cys Val Tyr
             35                  40                  45

Met Asn Gln Trp Tyr Ser Gln Cys Gln Pro Gly Ala Ser Ser Ser Asn
         50                  55                  60

Pro Pro Ser Asn Ala Ser Asn Asn Asn Asn Asp Asn Asn
 65                  70                  75                  80

Asn Asn Asn Asn Asn Asn Asn Asn Asn Asn Asn Asn Asn Asn
                 85                  90                  95

Asn Asn Ser Gly Ser Gly Ser Thr Gln Asn Phe Phe Thr Asn Gln Ile
            100                 105                 110
```

```
Tyr Ala Asn Pro Lys Phe Ile Glu Glu Val Asn Ser Ile Pro Lys
        115                 120                 125

Leu Ser Trp Asp Leu Gln Gln Lys Ala Gln Lys Val Lys Asp Val Pro
130                 135                 140

Thr Ala Val Trp Leu Ala Trp Glu Gly Ala Pro Gly Glu Val Glu Gln
145                 150                 155                 160

His Leu Lys Ala Ala Gly Ser Lys Thr Val Phe Ile Leu Tyr Met
                165                 170                 175

Ile Pro Thr Arg Asp Cys Asn Ser Asn Ala Ser Ala Gly Gly Ala Gly
        180                 185                 190

Ser Leu Asn Thr Tyr Lys Gly Tyr Val Asp Asn Ile Ser Arg Thr Ile
        195                 200                 205

Arg Ser Tyr Pro Asn Ser Lys Val Val Met Val Leu Glu Pro Asp Thr
210                 215                 220

Leu Gly Asn Leu Val Thr Gly Asn Ser Ala Asn Cys Gln Asn Val Arg
225                 230                 235                 240

Gln Leu His Lys Asn Ala Leu Ser Tyr Ala Val Asn Val Tyr Gly Ala
                245                 250                 255

Met Asn Asn Val Ser Val Tyr Leu Asp Ala Ala His Gly Lys Trp Leu
        260                 265                 270

Gly Gly Val Thr Asp Lys Val Ala Ala Val Val Lys Glu Ile Leu Asn
        275                 280                 285

Asn Ala Pro Asn Gly Lys Ile Arg Gly Leu Ser Thr Asn Val Ser Asn
        290                 295                 300

Tyr Gln Pro Ile Ala Ser Glu Tyr Ser Tyr His Gln Lys Leu Ala Ser
305                 310                 315                 320

Ser Leu Ser Ala Val Gly Ile Pro Asn Met His Phe Ile Val Asp Thr
                325                 330                 335

Gly Arg Asn Gly Val Asp Val Ser Ala Ala Phe Asn Thr Ser Glu Thr
        340                 345                 350

Trp Cys Asn Phe Val Gly Thr Gly Phe Gly Glu Arg Pro Arg Gly Asn
        355                 360                 365

Pro Asn Ser Gly Met Pro Leu Leu Asp Ala Tyr Met Trp Leu Lys Thr
370                 375                 380

Pro Arg Glu Ser Asp Gly Ser Ser Ser Gly Ser Arg Ala Asp Pro Val
385                 390                 395                 400

Cys Ser Arg Ser Asp Ser Leu Arg Gly Ala Pro Asp Ala Gly Gln Trp
                405                 410                 415

Phe His Asp Tyr Phe Val Gln Leu Leu Arg Asn Ala Arg Pro Gly Phe
        420                 425                 430

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:oligonucleotide

<400> SEQUENCE: 3
atgaaaattt tacttttgc cag                                              23

<210> SEQ ID NO 4
<211> LENGTH: 23
<212> TYPE: DNA
<213> ORGANISM: Artificial Sequence
<220> FEATURE:
```

-continued

<223> OTHER INFORMATION: Description of Artificial Sequence:oligonucleotide

<400> SEQUENCE: 4
ttagaatcct ggtctagcat ttc                                               23

<210> SEQ ID NO 5
<211> LENGTH: 428
<212> TYPE: PRT
<213> ORGANISM: Neocallimastix patriciarum

<400> SEQUENCE: 5

Met Lys Asn Leu Leu Leu Ala Ser Val Leu Ser Gly Leu Ala Gly
 1               5                  10                  15

Leu Ala Asn Ala Ala Cys Gly Gly Ala Trp Ala Gln Cys Gly Gly Glu
            20                  25                  30

Asn Phe His Gly Asp Lys Cys Cys Val Ser Gly His Thr Cys Val Ser
        35                  40                  45

Ile Asn Gln Trp Tyr Ser Gln Cys Gln Pro Gly Gly Ala Pro Ser Asn
    50                  55                  60

Asn Ala Ser Asn Asn Asn Asn Asn Asn Asn Asn Asn Asn Asn
65                  70                  75                  80

Asn Asn Asn Asn Asn Asn His Asn Asn Asn Asn Asn Asn Asn Asn
                85                  90                  95

Asn Asn Asn Gly Gly Ser Gly Ser Thr Lys Asn Phe Phe Asp Asn Gln
            100                 105                 110

Ile Tyr Ala Asn Pro Lys Phe Ile Glu Glu Val Asn Ser Ser Ile Pro
        115                 120                 125

Arg Leu Ser Tyr Asp Leu Gln Gln Lys Ala Gln Lys Val Lys Asn Val
    130                 135                 140

Pro Thr Ala Val Trp Leu Ala Trp Asp Gly Ala Thr Gly Glu Val Ala
145                 150                 155                 160

Gln His Leu Lys Ala Ala Gly Ser Lys Thr Val Val Phe Ile Met Tyr
                165                 170                 175

Met Ile Pro Thr Arg Asp Cys Asn Ala Asn Ala Ser Ala Gly Gly Ala
            180                 185                 190

Gly Asn Leu Asn Thr Tyr Lys Gly Tyr Val Asp Asn Ile Ala Arg Thr
        195                 200                 205

Ile Arg Ser Tyr Pro Asn Ser Lys Val Val Met Ile Leu Glu Pro Asp
    210                 215                 220

Thr Leu Gly Asn Leu Val Thr Ala Asn Ser Ala Asn Cys Gln Asn Val
225                 230                 235                 240

Arg Asn Leu His Lys Asn Ala Leu Ser Tyr Gly Val Asn Val Phe Gly
                245                 250                 255

Ser Met Ser Asn Val Ser Val Tyr Leu Asp Ala Ala His Gly Ala Trp
            260                 265                 270

Leu Gly Ser Ser Thr Asp Lys Val Ala Ser Val Val Lys Glu Ile Leu
        275                 280                 285

Asn Asn Ala Pro Asn Gly Lys Ile Arg Gly Leu Ser Thr Asn Ile Ser
    290                 295                 300

Asn Tyr Gln Ser Ile Ser Ser Glu Tyr Gln Tyr His Gln Lys Leu Ala
305                 310                 315                 320

Ser Ala Leu Ala Ala Val Gly Val Pro Asn Met His Phe Ile Val Asp
                325                 330                 335

Thr Gly Arg Asn Gly Val Thr Ile Asn Ser Gly Thr Trp Cys Asn Leu
        340                 345                 350

-continued

```
Val Gly Thr Gly Leu Gly Glu Arg Pro Arg Gly Asn Pro Asn Ala Gly
            355                 360                 365

Met Pro Leu Leu Asp Ala Tyr Met Trp Leu Lys Thr Pro Gly Glu Ser
    370                 375                 380

Asp Gly Ser Ser Gly Ser Arg Ala Asp Pro Asn Cys Ser Ser Asn
385                 390                 395                 400

Asp Ser Leu Arg Gly Ala Pro Asp Ala Gly Gln Trp Phe His Asp Tyr
                405                 410                 415

Phe Ala Gln Leu Val Arg Asn Ala Arg Pro Ser Phe
            420                 425

<210> SEQ ID NO 6
<211> LENGTH: 459
<212> TYPE: PRT
<213> ORGANISM: Orpinomyces sp. PC-2

<400> SEQUENCE: 6

Met Lys Phe Ser Thr Val Leu Ala Thr Leu Phe Ala Thr Gly Ala Leu
 1               5                  10                  15

Ala Ser Glu Cys His Trp Gln Tyr Pro Cys Cys Lys Asp Cys Thr Val
             20                  25                  30

Tyr Tyr Thr Asp Thr Glu Gly Lys Trp Gly Val Leu Asn Asn Asp Trp
         35                  40                  45

Cys Met Ile Asp Asn Arg Arg Cys Ser Ser Asn Asn Asn Cys Ser
     50                  55                  60

Ser Ser Ile Thr Ser Gln Gly Tyr Pro Cys Cys Ser Asn Asn Cys
 65                  70                  75                  80

Lys Val Glu Tyr Thr Asp Asn Asp Gly Lys Trp Gly Val Glu Asn Asn
                 85                  90                  95

Asn Trp Cys Gly Ile Ser Asn Ser Cys Gly Gly Gln Gln Gln Gln
            100                 105                 110

Pro Thr Gln Pro Thr Gln Pro Thr Gln Pro Gln Gln Pro Thr Gln Pro
            115                 120                 125

Ser Ser Asp Asn Phe Phe Glu Asn Glu Ile Tyr Ser Asn Tyr Lys Phe
130                 135                 140

Gln Gly Glu Val Asp Ile Ser Ile Lys Lys Leu Asn Gly Asp Leu Lys
145                 150                 155                 160

Ala Lys Ala Glu Lys Val Lys Tyr Val Pro Thr Ala Val Trp Leu Ala
                165                 170                 175

Trp Asp Gly Ala Pro Gln Glu Val Pro Arg Tyr Leu Gln Glu Ala Gly
            180                 185                 190

Asn Lys Thr Val Val Phe Val Leu Tyr Met Ile Pro Thr Arg Asp Cys
        195                 200                 205

Gly Ala Asn Ala Ser Ala Gly Gly Ser Ala Thr Ile Asp Lys Tyr Lys
    210                 215                 220

Gly Tyr Ile Asn Asn Ile Tyr Asn Thr Ser Asn Gln Tyr Lys Asn Ser
225                 230                 235                 240

Lys Ile Val Met Ile Leu Glu Pro Asp Thr Ile Gly Asn Leu Val Thr
                245                 250                 255

Asn Asn Asn Asp Asn Cys Arg Asn Val Arg Asn Met His Lys Gln Ala
            260                 265                 270

Leu Ser Tyr Ala Ile Ser Lys Phe Gly Thr Gln Ser His Val Lys Val
        275                 280                 285

Tyr Leu Asp Ala Ala His Gly Ala Trp Leu Asn Gln Tyr Ala Asp Gln
```

```
            290                 295                 300
Thr Ala Asn Val Ile Lys Glu Ile Leu Asn Asn Ala Gly Ser Gly Lys
305                 310                 315                 320

Leu Arg Gly Ile Ser Thr Asn Val Ser Asn Tyr Gln Ser Ile Glu Ser
                325                 330                 335

Glu Tyr Lys Tyr His Gln Asn Leu Asn Arg Ala Leu Glu Ser Lys Gly
            340                 345                 350

Val Arg Gly Leu Lys Phe Ile Val Asp Thr Ser Arg Asn Gly Ala Asn
            355                 360                 365

Val Glu Gly Ala Phe Asn Ala Ser Gly Thr Trp Cys Asn Phe Lys Gly
        370                 375                 380

Ala Gly Leu Gly Gln Arg Pro Lys Gly Asn Pro Asn Pro Gly Ser Met
385                 390                 395                 400

Pro Leu Leu Asp Ala Tyr Met Trp Ile Lys Thr Pro Gly Glu Ala Asp
                405                 410                 415

Gly Ser Ser Gln Gly Ser Arg Ala Asp Pro Val Cys Ala Arg Gly Asp
            420                 425                 430

Ser Leu Gln Gly Ala Pro Asp Ala Gly Ser Trp Phe His Glu Tyr Phe
            435                 440                 445

Thr Met Leu Ile Gln Asn Ala Asn Pro Pro Phe
450                 455
```

<210> SEQ ID NO 7
<211> LENGTH: 449
<212> TYPE: PRT
<213> ORGANISM: Orpinomyces sp. PC-2

<400> SEQUENCE: 7

```
Met Lys Phe Ser Ala Leu Ile Ser Thr Leu Phe Ala Ala Gly Ala Met
1               5                   10                  15

Ala Ser Arg Cys His Pro Ser Tyr Pro Cys Cys Asn Gly Cys Asn Val
                20                  25                  30

Glu Tyr Thr Asp Thr Glu Gly Asn Trp Gly Val Glu Asn Phe Asp Trp
            35                  40                  45

Cys Phe Ile Asp Glu Ser Arg Cys Asn Pro Gly Tyr Cys Lys Phe Glu
        50                  55                  60

Ala Leu Gly Tyr Ser Cys Cys Lys Gly Cys Glu Val Val Tyr Ser Asp
65                  70                  75                  80

Glu Asp Gly Asn Trp Gly Val Glu Asn Gln Gln Trp Cys Gly Ile Arg
                85                  90                  95

Asp Asn Cys Thr Pro Asn Val Pro Ala Thr Ser Ala Arg Thr Thr Thr
                100                 105                 110

Arg Thr Thr Thr Thr Thr Arg Thr Thr Thr Val Asn Ser Leu Pro Thr
            115                 120                 125

Ser Asp Asn Phe Phe Glu Asn Glu Leu Tyr Ser Asn Tyr Lys Phe Gln
130                 135                 140

Gly Glu Val Asp Gln Ser Ile Gln Arg Leu Ser Gly Ser Leu Gln Glu
145                 150                 155                 160

Lys Ala Lys Lys Val Lys Tyr Val Pro Thr Ala Ala Trp Leu Ala Trp
                165                 170                 175

Ser Gly Ala Thr Asn Glu Val Ala Arg Tyr Leu Asn Glu Ala Gly Ser
            180                 185                 190

Lys Thr Val Val Phe Val Leu Tyr Met Ile Pro Thr Arg Asp Cys Asn
        195                 200                 205
```

```
Ala Gly Gly Ser Asn Gly Gly Ala Asp Asn Leu Ser Thr Tyr Gln Gly
    210                 215                 220

Tyr Val Asn Ser Ile Tyr Asn Thr Ile Asn Gln Tyr Pro Asn Ser Arg
225                 230                 235                 240

Ile Val Met Ile Ile Glu Pro Asp Thr Ile Gly Asn Leu Val Thr Ala
                    245                 250                 255

Asn Asn Ala Asn Cys Arg Asn Val His Asp Met His Lys Gln Ala Leu
                260                 265                 270

Ser Tyr Ala Ile Ser Lys Phe Gly Thr Gln Lys Asn Val Arg Val Tyr
        275                 280                 285

Leu Asp Ala Ala His Gly Gly Trp Leu Asn Ser Ser Ala Asp Arg Thr
    290                 295                 300

Ala Glu Val Ile Ala Glu Ile Leu Arg Asn Ala Gly Asn Gly Lys Ile
305                 310                 315                 320

Arg Gly Ile Ser Thr Asn Val Ser Asn Tyr Gln Pro Val Tyr Ser Glu
                    325                 330                 335

Tyr Gln Tyr His Gln Asn Leu Asn Arg Ala Leu Glu Ser Arg Gly Val
                340                 345                 350

Arg Gly Met Lys Phe Ile Val Asp Thr Ser Arg Asn Gly Arg Asn Pro
        355                 360                 365

Ser Ser Ala Thr Trp Cys Asn Leu Lys Gly Ala Gly Leu Gly Ala Arg
    370                 375                 380

Pro Gln Ala Asn Pro Asp Pro Asn Met Pro Leu Leu Asp Ala Tyr Val
385                 390                 395                 400

Trp Ile Lys Thr Pro Gly Glu Ser Asp Ser Ala Ser Ser Ala Asp Pro
                    405                 410                 415

Val Cys Arg Asn Ser Asp Ser Leu Gln Gly Ala Pro Ala Ala Gly Ser
                420                 425                 430

Trp Phe His Asp Tyr Phe Val Met Leu Leu Glu Asn Ala Asn Pro Pro
        435                 440                 445

Phe

<210> SEQ ID NO 8
<211> LENGTH: 470
<212> TYPE: PRT
<213> ORGANISM: Trichoderma reesei

<400> SEQUENCE: 8

Met Ile Val Gly Ile Leu Thr Thr Leu Ala Thr Leu Ala Thr Leu Ala
  1               5                  10                  15

Ala Ser Val Pro Leu Glu Glu Arg Gln Ala Cys Ser Ser Val Trp Gly
                 20                  25                  30

Gln Cys Gly Gly Gln Asn Trp Ser Gly Pro Thr Cys Cys Ala Ser Gly
             35                  40                  45

Ser Thr Cys Val Tyr Ser Asn Asp Tyr Tyr Ser Gln Cys Leu Pro Gly
         50                  55                  60

Ala Ala Ser Ser Ser Ser Ser Thr Arg Ala Ala Ser Thr Thr Arg Val
 65                  70                  75                  80

Ser Pro Thr Thr Ser Arg Ser Ser Ser Ala Thr Pro Pro Pro Gly Ser
                 85                  90                  95

Thr Thr Thr Arg Val Pro Pro Val Gly Ser Gly Thr Ala Thr Tyr Ser
                100                 105                 110

Gly Asn Pro Phe Val Gly Val Thr Pro Trp Ala Asn Ala Tyr Tyr Ala
            115                 120                 125
```

```
Ser Glu Val Ser Ser Leu Ala Ile Pro Ser Leu Thr Gly Ala Met Ala
        130                 135                 140

Thr Ala Ala Ala Val Ala Lys Val Pro Ser Phe Met Trp Leu Asp
145                 150                 155                 160

Thr Leu Asp Lys Thr Pro Leu Met Glu Gln Thr Leu Ala Asp Ile Arg
                165                 170                 175

Thr Ala Asn Lys Asn Gly Gly Asn Tyr Ala Gly Gln Phe Val Val Tyr
                180                 185                 190

Asp Leu Pro Asp Arg Asp Cys Ala Ala Leu Ala Ser Asn Gly Glu Tyr
                195                 200                 205

Ser Ile Ala Asp Gly Gly Val Ala Lys Tyr Lys Asn Tyr Ile Asp Thr
        210                 215                 220

Ile Arg Gln Ile Val Val Glu Tyr Ser Asp Ile Arg Thr Leu Leu Val
225                 230                 235                 240

Ile Glu Pro Asp Ser Leu Ala Asn Leu Val Thr Asn Leu Gly Thr Pro
                245                 250                 255

Lys Cys Ala Asn Ala Gln Ser Ala Tyr Leu Glu Cys Ile Asn Tyr Ala
        260                 265                 270

Val Thr Gln Leu Asn Leu Pro Asn Val Ala Met Tyr Leu Asp Ala Gly
        275                 280                 285

His Ala Gly Trp Leu Gly Trp Pro Ala Asn Gln Asp Pro Ala Ala Gln
        290                 295                 300

Leu Phe Ala Asn Val Tyr Lys Asn Ala Ser Ser Pro Arg Ala Leu Arg
305                 310                 315                 320

Gly Leu Ala Thr Asn Val Ala Asn Tyr Asn Gly Trp Asn Ile Thr Ser
                325                 330                 335

Pro Pro Ser Tyr Thr Gln Gly Asn Ala Val Tyr Asn Glu Lys Leu Tyr
                340                 345                 350

Ile His Ala Ile Gly Pro Leu Leu Ala Asn His Gly Trp Ser Asn Ala
        355                 360                 365

Phe Phe Ile Thr Asp Gln Gly Arg Ser Gly Lys Gln Pro Thr Gly Gln
        370                 375                 380

Gln Gln Trp Gly Asp Trp Cys Asn Val Ile Gly Thr Gly Phe Gly Ile
385                 390                 395                 400

Arg Pro Ser Ala Asn Thr Gly Asp Ser Leu Leu Asp Ser Phe Val Trp
                405                 410                 415

Val Lys Pro Gly Gly Glu Cys Asp Gly Thr Ser Asp Ser Ser Ala Pro
                420                 425                 430

Arg Phe Asp Ser His Cys Ala Leu Pro Asp Ala Leu Gln Pro Ala Pro
                435                 440                 445

Gln Ala Gly Ala Trp Phe Gln Ala Tyr Phe Val Gln Leu Leu Thr Asn
        450                 455                 460

Ala Asn Pro Ser Phe Leu
465                 470

<210> SEQ ID NO 9
<211> LENGTH: 461
<212> TYPE: PRT
<213> ORGANISM: Fusarium oxysporum

<400> SEQUENCE: 9

Met Ala Tyr Lys Leu Ile Leu Ala Ala Phe Ala Ala Thr Ala Leu Ala
 1               5                  10                  15

Ala Pro Val Glu Glu Arg Gln Ser Cys Ser Asn Gly Val Trp Ala Gln
            20                  25                  30
```

```
Cys Gly Gly Gln Asn Trp Ser Gly Thr Pro Cys Cys Thr Ser Gly Asn
         35                  40                  45

Lys Cys Val Lys Leu Asn Asp Phe Tyr Ser Gln Cys Gln Pro Gly Ser
         50                  55                  60

Ala Glu Pro Ser Ser Thr Ala Ala Gly Pro Ser Ser Thr Thr Ala Thr
     65                  70                  75                  80

Lys Thr Thr Ala Thr Gly Gly Ser Ser Thr Thr Ala Gly Gly Ser Val
                 85                  90                  95

Thr Ser Ala Pro Pro Ala Ala Ser Asp Asn Pro Tyr Ala Gly Val Asp
             100                 105                 110

Leu Trp Ala Asn Asn Tyr Tyr Arg Ser Glu Val Met Asn Leu Ala Val
             115                 120                 125

Pro Lys Leu Ser Gly Ala Lys Ala Thr Ala Ala Lys Val Ala Asp
     130                 135                 140

Val Pro Ser Phe Gln Trp Met Asp Thr Tyr Asp His Ile Ser Leu Met
145                 150                 155                 160

Glu Asp Thr Leu Ala Asp Ile Arg Lys Ala Asn Lys Ala Gly Gly Lys
                 165                 170                 175

Tyr Ala Gly Gln Phe Val Val Tyr Asp Leu Pro Asn Arg Asp Cys Ala
                 180                 185                 190

Ala Ala Ala Ser Asn Gly Glu Tyr Ser Leu Asp Lys Asp Gly Ala Asn
             195                 200                 205

Lys Tyr Lys Ala Tyr Ile Ala Lys Ile Lys Gly Ile Leu Gln Asn Tyr
     210                 215                 220

Ser Asp Thr Lys Val Ile Leu Val Ile Glu Pro Asp Ser Leu Ala Asn
225                 230                 235                 240

Leu Val Thr Asn Leu Asn Val Asp Lys Cys Ala Lys Ala Glu Ser Ala
                 245                 250                 255

Tyr Lys Glu Leu Thr Val Tyr Ala Ile Lys Glu Leu Asn Leu Pro Asn
             260                 265                 270

Val Ser Met Tyr Leu Asp Ala Gly His Gly Gly Trp Leu Gly Trp Pro
     275                 280                 285

Ala Asn Ile Gly Pro Ala Ala Lys Leu Tyr Ala Gln Ile Tyr Lys Asp
     290                 295                 300

Ala Gly Lys Pro Ser Arg Val Arg Gly Leu Val Thr Asn Val Ser Asn
305                 310                 315                 320

Tyr Asn Gly Trp Lys Leu Ser Thr Lys Pro Asp Tyr Thr Glu Ser Asn
                 325                 330                 335

Pro Asn Tyr Asp Glu Gln Arg Tyr Ile Asn Ala Phe Ala Pro Leu Leu
             340                 345                 350

Ala Gln Glu Gly Trp Ser Asn Val Lys Phe Ile Val Asp Gln Gly Arg
             355                 360                 365

Ser Gly Lys Gln Pro Thr Gly Gln Lys Ala Gln Gly Asp Trp Cys Asn
     370                 375                 380

Ala Lys Gly Thr Gly Phe Gly Leu Arg Pro Ser Thr Asn Thr Gly Asp
385                 390                 395                 400

Ala Leu Ala Asp Ala Phe Val Trp Val Lys Pro Gly Gly Glu Ser Asp
```

-continued

```
                        405                 410                 415
Gly Thr Ser Asp Thr Ser Ala Ala Arg Tyr Asp Tyr His Cys Gly Leu
            420                 425                 430

Asp Ala Leu Lys Pro Ala Pro Glu Ala Gly Thr Trp Phe Gln Ala Tyr
        435                 440                 445

Phe Glu Gln Leu Leu Asp Asn Ala Asn Pro Ser Phe Leu
    450                 455                 460
```

ORPINOMYCES CELLULASE CELF PROTEIN AND CODING SEQUENCES

ACKNOWLEDGEMENT OF FEDERAL RESEARCH SUPPORT

This invention was made, at least in part, with funding from the United States Department of Energy (Grant No. DE-FG05 93ER 20127). Accordingly, the United States Government has certain rights in this invention.

CROSS REFERENCE TO RELATED APPLICATIONS not applicable

BACKGROUND OF THE INVENTION

The field of the present invention is the area of cellulolytic enzymes, nucleotide sequences encoding them and recombinant host cells and methods for producing them.

Cellulosic biomass, photosynthesized by solar energy with $CO_2$ and $H_2O$, is one of the most important renewable energy resources on earth. Its effective utilization through biological processes is one approach to overcoming the shortage of foods, feeds and fuels, expected as a consequence of the explosive increase in human population [Ohmiya et al. (1997) *Biotechnol. Gen. Engineer. Rev.* 14, 365–414]. Several types of enzymes are required for complete hydrolysis of cellulose to glucose, including endoglucanase, exoglucanase or cellobiohydrolase and β-glucosidase [Filho 1996) *Can. J. Microbiol.* 42, 1–5].

There is a need in the art for cellulolytic enzymes, for DNA encoding the CelF cellulase of Orpinomyces PC-2 and for methods which enable producing the CelF cellulase in recombinant host cells. Cellulases are useful in the textile and paper industries, as well as in the fuel and chemical production from cellulosic feedstocks.

SUMMARY OF THE INVENTION

This invention provides a novel cellulase (CelF) from Orpinomyces sp. PC-2. CelF has endoglucanase activity, producing primarily cellobiose from cellotetraose or cellopentaose, and glucose and cellobiose from cellotriose.

This invention provides a substantially pure mature cellulase protein termed "CelF" of Orpinomyces PC-2. Mature CelF has an amino acid sequence as given in Table 3, or SEQ ID NO:2, from amino acid 22 through 432 or an amino acid sequence having at least 85% sequence identity thereto and similar enzymatic properties. This cellulase is useful for degrading cellulosic material, for example, in the textile industry, in the paper industry and in the production of ethanol.

The CelF protein from Orpinomyces PC-2 has a calculated molecular weight of 46,736 kDa; however the CelF polypeptide of this invention includes proteins or polypeptides having the same or equivalent amino acid sequence.

The term CelF refers to the mature protein or polypeptide having the sequence given in SEQ ID NO:2 herein, equivalent sequences as defined below, and such sequences preceded with a methionine residue immediately preceding the listed sequence.

A chemically synthesized CelF polypeptide protein is considered an "isolated" protein.

CelF as used herein refers to a polypeptide product which exhibits similar biological activities, i.e., has similar specific activity to natural CelF isolated from Orpinomyces PC-2 or chemically synthesized in accordance with the sequence provided in SEQ ID NO:2 as measured in recognized bioassays, and has substantially the same or "equivalent" amino acid sequence as native CelF (SEQ ID NO:2). It will be understood that polypeptides deficient in one or more amino acids in the amino acid sequence reported herein for naturally occurring CelF, or polypeptides in which one or more amino acids in the amino acid sequence of natural CelF are replaced by other amino acids are within the scope of the invention and have "equivalent" sequences to that given in SEQ ID NO:2, provided that they exhibit the functional activity of CelF. This invention is intended to embrace all the allelic variations of CelF. Moreover, as noted above, derivatives obtained by simple modification of the amino acid sequence of the naturally-occurring product, e.g., by way of site-directed mutagenesis or other standard procedures, are included within the scope of the present invention. Forms of CelF produced by proteolysis of host cells that exhibit similar biological activities to mature, naturally-occurring CelF are also encompassed by the present invention. The present specification provides guidance to the skilled worker for preparing a large number of equivalent sequences which preferably do not alter areas of homology shared with other cellulases.

This invention also provides for genomic DNA and cDNA and for non-naturally occurring recombinant DNA molecules encoding the mature CelF protein or polypeptide and/or a signal peptide. The gene encoding CelF is termed celF herein. The DNA sequence encoding this protein from Orpinomyces is given in Table 3, SEQ ID NO:1, from nucleotide 95 to 1504, including the signal peptide which mediates secretion and an intron (nucleotides 187 to 297 of SEQ ID NO:1). The celF gene is useful for recombinantly expressing the CelF mature protein in *Escherichia coli* or other host cells.

It is recognized by those skilled in the art that the DNA sequences may vary due to the degeneracy of the genetic code and codon usage. All DNA sequences which encode the CelF polypeptide and/or signal peptide are included in this invention, including DNA sequences (as given in SEQ ID NO:1 from 95 to 1504, including the translation termination codon and the intron from nucleotides 187 to 297) having an ATG preceding the coding region for the mature protein.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the CelF mature protein coding region and CelF signal sequence coding region. The skilled artisan will 10 understand that the amino acid sequence of the exemplified CelF polypeptide and signal peptide can be used to identify and isolate additional, nonexemplified nucleotide sequences which will encode functional equivalents to the polypeptides defined by the amino acid sequences given in SEQ ID NO:1, or an amino acid sequence of greater than 90% identity thereto and having equivalent biological activity. DNA sequences having at least about 85% homology to the DNA sequences of SEQ ID NO:1 and encoding polypeptides with the same function are considered equivalent to the sequences of SEQ ID NO:1 and are included in the definition of "DNA encoding the CelF mature protein," the celF gene" and "the CelF signal peptide coding region," respectively. Following the teachings herein, the skilled worker will be able to make a large number of operative embodiments having equivalent DNA sequences to those listed herein.

The CelF coding sequences, including or excluding that encoding a signal peptide of this invention can be used to express the cellulase of the present invention in fungal host cells as, well as in bacteria, including without limitation, Bacillus spp and *E. coli*. Any host cell in which the signal sequence is expressed and processed may be used. Preferred eukaryotic host cells are Aureobasidium species, Aspergillus species, Trichoderma species and *Saccharomyces cerevisiae*, as well as other yeasts known to the art for fermentation, including *Pichia pastoris* (Sreekrishna, K. (1993) in Baltz, R. H., et al. (eds.) Industrial Microorganisms: Basic and Applied Molecular Genetics, ASM Press, Washington, DC 119–126; Glick, B. R. and Pasternak J. J. (1994) ASM Press (1994) Washington, DC. Filamentous fungi such as Aspergillus, Trichoderma, Penicillium, etc. are also useful host organisms for expression of the DNA of this invention (Van den Handel, C. et al. (1991) In: Bennett, J. W. and Lasure, L. L. (eds.), More Gene Manipulations in Fungi, Academic Press, Inc., New York, 397–428).

In addition the coding region for both the signal peptide and the mature CelF protein may be expressed in such hosts. Alternatively, the CelF mature protein coding region isolated from the signal sequence may be expressed in such hosts, or the coding region for the signal peptide isolated from the mature protein coding region may be expressed in such hosts.

In a preferred embodiment, vectors suitable for transformation of the host, preferably *S. cerevisiae*, with the celF gene, cDNA coding for the CelF mature protein, or the CelF signal peptide cDNA coding sequence in combination with a suitable foreign gene expressible in *S. cerevisiae*, are prepared with the gene under control of a promoter expressible in the host, preferably *S. cerevisiae*. Preferably sequences from SEQ ID NO:1 which are 5' to the coding region for the signal peptide are deleted from such constructs. Preferably the promoter is a constitutive promoter such as the yeast enolase promoter (Sangadala et al. (1994) In: Abstracts of University System of Georgia 1994 Research Symposium: Advances in Biotechnology, Georgia State University, Atlanta, Ga.) or the yeast alcohol dehydrogenase promoter (Pacitti et al. (1994) Biochimica et Biophysica Acta 1222:277–286). The vector is used to transform the host either by integration into the chromosome or otherwise. The host organism is then cultured under conditions allowing expression of the gene and the product recovered from the culture medium.

BRIEF DESCRIPTION OF THE DRAWINGS

FIGS. 1A–1B show alignment of the amino acid sequence of the Orpinomyces PC-2 CelF with the amino acid sequences of other family 6 cellulases, including CelA (SEQ ID NO:5) of *N. patriciarum* (Cela_Neoca) [Denman et al. (1996) *Appl. Environ. Microbiol.* 62, 1889–1896], CelA (SEQ ID NO:6) and CelC (SEQ ID NO:7) of Orpinomyces PC-2 (CelA_Orpin and CelC_Orpin) [Li et al. (1997) *Appl. Environ. Microbiol.* 63, 4721–4728], CBHIIs of *T. reesei* (Cbhii_Tri) (SEQ ID NO:8) [Teeri et al. (1987) *Gene* 51, 43–52], and *Fusarium oxysporum* (Cbhii_Fasar) (SEQ ID NO:9) [Sheppard et al. (1994) *Gene* 150, 163–167]. Gaps are introduced to optimize alignment, and gaps are treated as mismatches in the comparison of other amino acid sequences to that of Orpinomyces PC-2 CelF (SEQ ID NO:2).

DETAILED DESCRIPTION OF THE INVENTION

Figure 2:
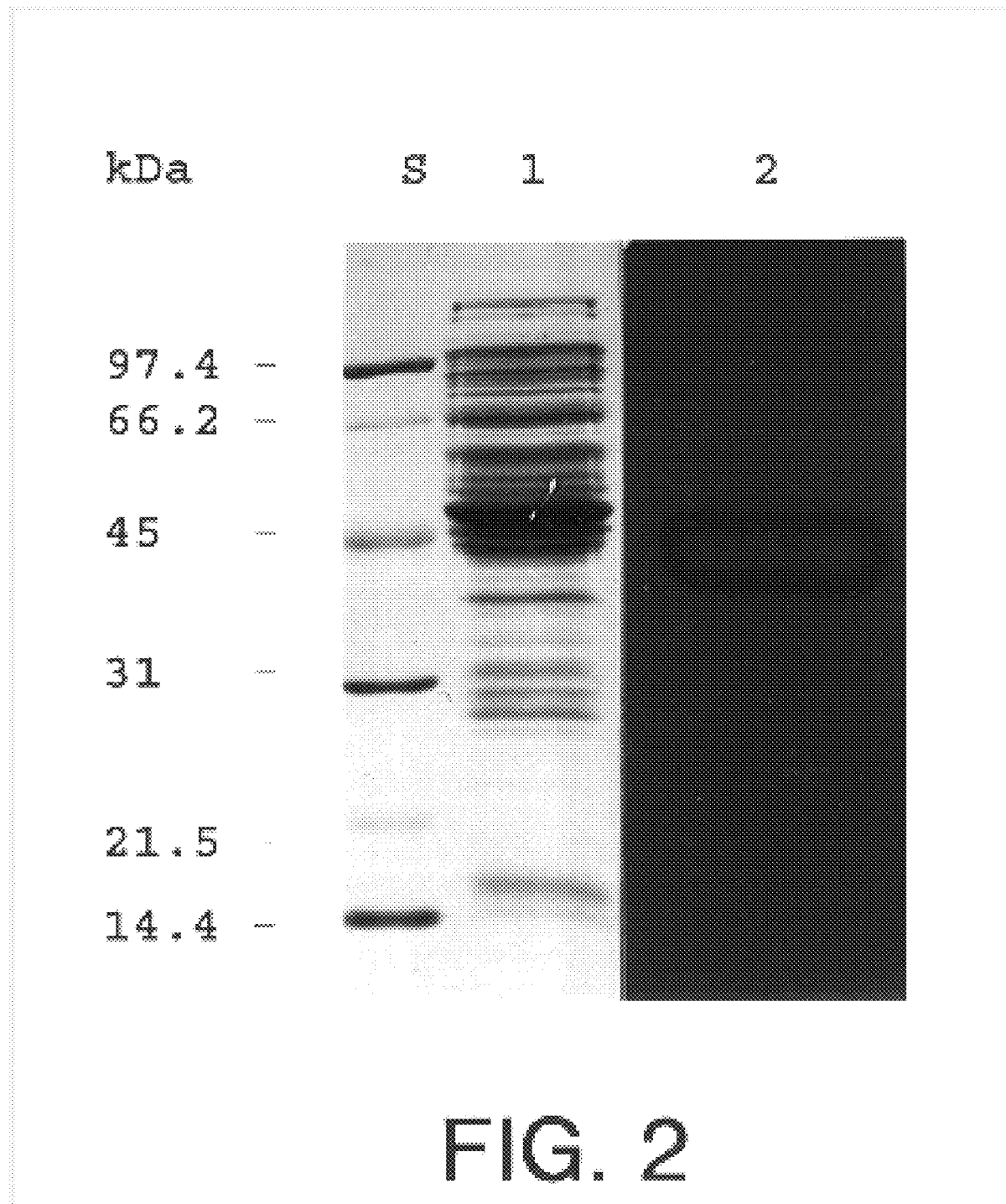
FIG. 2 illustrates SDS-PAGE and a zymogram of the recombinant CelF. Lane 1, Coomassie brilliant blue staining (50 μg protein); lane 2. zymogram gel; lane S, protein molecular mass standards.

The amino acids which occur in the various amino acid sequences referred to in the specification have their usual three- and one-letter abbreviations routinely used in the art A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Trp, Tryptophan; and Y, Tyr, Tyrosine.

Additional abbreviations used in the present specification include the following: aa, amino acid(s); bp, base pair(s); CD, catalytic domain(s); cDNA, DNA complementary to RNA; GCG, Genetics Computer Group, Madison, Wis.; CMC, carboxymethyl cellulose; CMCase, carboxymethyl cellulase; FPase, filter paper-ase; HMWC, high-molecular weight complex(es); IPTG, isopropyl-β-D-thiogalactoside; OSX, oat spelt xylan; ORF, open reading frame; RBB, remazol brilliant blue; RP, repeated peptide(s); pfu, plaque forming units.

Anaerobic fungi are part of the natural microflora of the alimentary tract of many herbivorous animals. Since the first anaerobic fungus, *Neocallimastix frontalis*, was isolated from the rumen of sheep [Orpin, G. C. (1975) *J. Gen. Microbiol.* 91, 249–262], at least 17 different anaerobic fungi have been isolated from ruminant and nonruminant herbivores. Anaerobic fungi produce highly active hydrolytic enzymes [Borneman et al. (1989) *Appl. Environ. Microbiol.* 55, 1066–1073], such as endoglucanases, xylanases, lichenase, and esterases, they physically associate with the lignocellulosic tissue of plant fragments, and their hyphae penetrate the plant tissue in vivo [Akin et al. (1983) *Appl. Environ. Microbiol.* 46, 738–748; Thedorou et al. (1996) *Proc. Nutr. Soc.* 55, 913–926], indicating that they are involved in degradation of plant biomass and play an important role in the rumen ecosystem. Several genes coding for the hydrolytic enzymes have been cloned and sequenced from the monocentric fungi *N. patriciarum* [Black et al. (1994) *Biochem. J.* 299, 381–387; Dalrymple et al. (1997) *Microbiology* 143, 2605–2614; Gilbert et al. (1992) *Mol. Microbiol.* 6, 2065–2072; Zhou et al. (1994) *Biochem. J.* 297, 359–364] *N. frontalis* [Durand et al. (1996) *Curr. Genet.* 30, 531–540] and Piromyces sp. [Fanutti et al. (1995) *J. Biol. Chem.* 270,29314–29322; Millward-Sadler et al. (1996) FEMS Microbiol. Letts. 141, 183–188] and from the polycentric fungi Orpinomyces PC-2 [Chen et al. (1997) *J. Bacteriol.* 179, 6028–6034; Chen et al. (1998) *FEMS Microbiol. Letts.* 159, 63–68; Li et al. (1997) *Appl. Environ. Microbiol.* 63, 628–635; Liu et al. (1997) *Appl. Environ. Microbiol.* 63, 4721–4728] and *Orpinomyces joyonii* [Liu et al. (1997) *Can. J. Microbiol.* 43, 477–485]. Analyses of the primary structures of endoglucanases, xylanases, and lichenase from the anaerobic fungi have revealed that there are substantial sequence homologies between genes from the rumen anaerobic fungi and from genes of bacteria of the rumen, which suggests that these genes have bacterial origin [Black et al. (1994) *Biochem. J.* 299, 381–387; Chen et al. (1997) *J. Bacteriol.* 179, 6028–6034; Chen et al. (1998) *FEMS Microbiol. Letts.* 159, 63–68; Gilbert et al. (1992) *Mol. Microbiol.* 6, 2065–2072; Li et al. (1997) *Appl. Environ. Microbiol.* 63, 628–635; Zhou et al. (1994) *Biochem. J.* 297, 359–364]. However, recently several cellobiohydrolase II (CBHII) type genes have been isolated from *N. patriciarum* [Denman et al. (1996) *Appl. Environ. Microbiol* 62, 1889–1896] and Orpinomyces PC-2 [Li et al. (1997) *Appl. Environ. Microbiol.* 63, 4721–4728]. Their primary structures are similar to those of aerobic filamentous fungi. An enolase gene from *N. frontalis* which contains an intron [Durand et al. (1995) *Microbiology* 141, 1301–1308] and a cyclophilin gene from Orpinomyces PC-2 which is heavily interrupted by introns have been reported. But no intron has been found in any previously examined genes coding for hydrolytic enzymes of the anaerobic fungi [Chen et al. (1997) *J. Bacteriol.* 179, 6028–6034; Chen et al. (1998) *FEMS Microbiol. Letts.* 159, 63–68; Li et al. (1997) *Appl. Environ. Microbiol.* 63, 628–635; Liu et al. (1997) *Can. J. Microbiol.* 43, 477–485; Zhou et al. (1994) *Biochem. J.* 297, 359–364].

Screening of an Orpinomyces PC-2 cDNA library constructed in λZAPII yielded twenty cellulase-producing plaques when 2×10⁵ pfu were plated. The positive plaques were further enriched and purified. PCR, restriction enzyme digestion, and sequencing analyses revealed that sixteen out of these plaques represented cDNAs of celA, celB, celC and celE which were reported previously [Chen et al. (1998) *FEMS Microbiol. Letts.* 159, 63–68; Li et al. (1997) *Appl. Environ. Microbiol.* 63, 628–635; Li et al. (1997) *Appl. Environ. Microbiol* 63, 4721–4728]. The other three plaques represented three different novel cellulase cDNAs (pCEL2, pCEL5 and pCEL8).

Sequence analysis of the inserts in the plasmids obtained from the plaques by in vivo excision revealed that pCEL8 contained a 1,520 bp cDNA (celF) with a complete open reading frame (ORF) (Table 3, SEQ ID NO:1) encoding a polypeptide (CelF) of 432 amino acids (SEQ ID NO:2) with a calculated mass of 46,736 Da. The translation start codon (ATG) for celF was assigned based on the facts that there were stop codons in all three frames preceding the ORF, and there was no ATG codon upstream of the ORF. After the ORF, a 3'untranslated AT-rich end of 127 bp was observed, but no typical long poly(A) stretch was found. The G+C content of the ORF of celF was 36.4% and that of the 5' and 3' noncoding regions was very low (11.8%). High A+T contents have been found also in other cDNAs from anaerobic fungi [Chen et al. (1997) *J. Bacteriol.* 179, 6028–6034; Chen et al. (1998) *FEMS Microbiol. Letts.* 159, 63–68; Li et al. (1997) *Appl. Environ. Microbiol.* 63, 628–635; Zhou et al. (1994) *Biochem. J.* 297, 359–364]. Although anaerobic fungal mRNA do not contain typical Shine-Dalgarno-like sequences for translation initiation, the sequence AGAACT, 6 bp upstream of the ATG start codon, may act as a ribosomal binding sequence. Similar sequences have been found in several genes of anaerobic fungi [Chen et al. (1997) *J. Bacteriol.* 179, 6028–6034; Gilbert et al. (1992) *Mol. Microbiol.* 6, 2065–2072]. These sequences have been suggested to function as weak ribosomal binding sequences in *E. coli*. The codon usage for celF is similar to other Orpinomyces PC-2 cellulase, xylanase, and lichenase genes [Chen et al. (1997) *J. Bacteriol.* 179, 6028–6034; Chen et al. (1998) *FEMS Microbiol. Letts.* 159, 63–68; Li et al. (1997) *Appl. Environ. Microbiol.* 63, 628–635; Li et al. (1997) *Appl. Environ. Microbiol.* 63, 4721–4728]. Twenty-one codons were not utilized and there was a marked preference for a T in the wobble position (59% of all codons contained T at this position).

Analysis of the domains of CelF (Table 3; SEQ ID NO:1, SEQ ID NO:2) revealed that it contains a typical signal peptide sequence consisting of 21 amino acid residues [Von Heijne, G. (1986) *Nucleic Acids Res.* 14, 4683–4690] as was found in CelA of *N. patriciarum* [Denman et al. (1996) *Appl. Environ. Microbiol.* 62, 1889–1896]. Immediately after the signal sequence, amino acid residues 22 to 57 (in Table 3) constitute a typical fungal cellulose binding domain (CBD) [Denman et al. (1996) supra; Gilkes et al. (1991) *Microbiol. Rev.* 55, 303–315]. The catalytic domain is located at the C-terminus (amino acid residues 106 to 432 in Table 3). It is separated from the CBD by an extremely Asn-rich linker (amino acid residues 67 to 105).

According to the classification of fungal CBDs [Tomme et al. (1995) p. 142–163. In J. N. Saddler and M. H. Penner (eds.), ACS Symposium series 618, American Chemical Society, Washington, DC], the CBD of CelF is placed in family 1, which is exclusive to fungal hydrolases. It has a high degree of homology with the CBD of CBHII from *Trichoderma reesei* (86% similarity and 53% identity). Six cysteine residues (numbers 22, 29, 39, 40, 46, and 56 in Table 3) forming three disulfide bridges stabilizing the polypeptide are conserved in CelF [Hoffrén et al. (1995) *Protein Eng.* 8, 443–450; Teeri et al. (1987) *Gene* 51, 43–52]. Three highly conserved aromatic residues (Tyr26, Trp52, and Tyr53) which are conspicuous building blocks of the flat face binding to the cellulose surface [Hoffrén et al. (1995) supra], were found in CelF. Moreover three invariant amino acids (Gln28, Asn50, and Gln55) in suitable positions for hydrogen bonding with the cellulose surface are also conserved in the CBD of CelF [Hoffrén et al. (1995) supra]. The presence of a CBD in CelF is consistent with the fact that about 70% of the CMCase activity of *E. coli* cell-free extracts adsorbed onto Avicel.

The deduced amino acid sequence of CelF (SEQ ID NO:2) of Orpinomyces PC-2, when compared with protein sequences in the SWISS PROT and GP data banks, was found to be significantly homologous with several anaerobic and aerobic fungal CBHIIs belonging to family 6 glycosyl hydrolases (FIGS. 1A–1B) [Henrissat, B., and A. Bairoch (1993) Biochem. J. 293, 781–788]. The highest identity was with CelA of N. patriciarum [Denman et al. (1996) Appl. Environ. Microbiol. 62, 1889–1896]. The identity with it was 82.9% when the complete sequences including signal peptide, CBD, linker, and catalytic domain were compared. One deletion and /or insertion between these two enzymes was found in the linker region (after residue 86 in CelF), whereas five amino acids (residues 345 to 349) present at carboxyl terminus of Orpinomyces PC-2 CelF are not found in N. patriciarum CelA. The catalytic domain of CelF of Orpinomyces PC-2 located at the C-terminal region starting with amino acid residues 106 is highly homologous with the catalytic domains of CelA (75.2% similarity; 64.8 identity) and CelC (74.9% similarity; 63.6% identity) of the same organism (Orpinomyces PC-2) [Li et al. (1997) Appl. Environ. Microbiol. 63, 4721–4728]. CelF also has substantial homology with the CBHIIs of T. reesei (52.6% similarity; 37.2% identity) [Teeri et al. (1987) Gene 51, 43–52] and Fusarium oxysporum (54.7% similarity; 38.9% identity) [Sheppard et al. (1994) Gene 150, 163–167].

The three-dimensional structure of the catalytic domain of T. reesei CBHII has been determined [Rouvinen et al. (1990) Science 249, 380–386]. Mutagenesis studies of Asp245, Asp199, and Tyr193 of T. reesei CBHII have shown that Asp245 is the likely proton donor in the catalytic event and the neighboring Asp199 is charged, ensuring the protonation of Asp245. A function of the Tyr193 is to modulate the protonation states of the interacting carboxylates of Asp199 and 245 [Koivula et al. (1996) Protein Eng. 9, 691–699]. These three amino acid residues are conserved in family 6 glycosyl hydrolases and are present in the catalytic domain of CelF (Asp181, Asp223, and Tyr175 in Table 3) and CelA and CelC [Li et al. (1997) Appl. Environ. Microbiol 63, 4721–4728].

Although the catalytic domain of CelF is very similar to those of CelA and CelC (FIGS. 1A–1B), CelF has a CBD, whereas CelA and CelC contain a noncatalytic repeated peptide domain (NCRPD), which is not involved in catalysis or cellulose binding [Black et al. (1994) Biochem. J. 299, 381–387; Gilbert et al. (1992) Mol. Microbiol. 6, 2065–2072; Li et al. (1997) Appl. Environ. Microbiol. 63, 4721–4728]. It has been suggested that NCRPDs function as docking domains in a fashion similar to that of the dockerin domains of catalytic subunits of the cellulosome of Clostridium thermocellum [Choi, S. -K., and L. G. Ljungdahl (1996) Biochemistry 35, 4906–4910; Fanutti et al. (1995) J. Biol. Chem. 270, 29314–29322; Pages et al. (1997) Proteins 29, 517–527]. The lack of an NCRPD in CelF suggests that enzyme is not a part of cellulase/hemicellulase complexes found in Orpinomyces PC-2 and other anaerobic fungi [Dijkerman et al. (1996) Appl. Environ. Microbiol. 62, 20–25; Wilson, C. A., and T. M. Wood (1992) Appl. Microbiol. Biotechnol. 37, 125–129].

CMCase activities were detected in E. coli cell-free extracts harboring the plasmid pCEL8 (celF). Zymogram analysis showed that the apparent molecular mass of CelF produced in E. coli was approximately 44 kDa (FIG. 2), which appears to be consistent with the deduced molecular mass of the mature CelF lacking the proposed signal peptide. No other activity band with lower molecular mass was detected, indicating that the poly-Asn linker region was relatively stable. This is in contrast with several other anaerobic fungal hydrolytic enzymes containing NCRPDs where the linker regions between the catalytic domains and NCRPDs are susceptible to truncation [Chen et al. (1998) FEMS Microbiol. Letts. 159, 63–68; Gilbert et al. (1992) Mol. Microbiol. 6, 2065–2072; Li et al. (1997) Appl. Environ. Microbiol. 63, 628–635].

Activities on various substrates of cell-free extracts of E. coli expressing Orpinomyces CelF are given in Table 1. The enzyme present in the extracts rapidly hydrolyze amorphous-swollen cellulose, CMC, barley $\beta$-glucan, and lichenin. The cell-free extracts containing CelF had a relatively high activity towards crystalline cellulose (Avicel) with a specific activity of 0.09 U/mg protein. No detectable hydrolysis was observed of pNP-$\beta$-D-glucoside, oat spelt xylan or pNP-$\beta$-D-xyloside. It seems that CelF had both endoglucanase and cellobiohydrolase activities which are similar to CelA and CelC from the same strain [Li et al. (1997) Appl. Environ. Microbiol. 63, 4721–4728], CelA from N. patriciarum [Denman et al. (1996) Appl. Environ. Microbiol. 62, 1889–1896], and CBHII from T. reesei [Van Tilbeurgh et al. (1984) FEBS Letts. 169, 215–218].

Hydrolysis products formed during the action of the recombinant CelF on cellooligosaccharides were determined by HPLC (Table 2). Cellobiose was not hydrolyzed, whereas cellotriose was slowly hydrolyzed to cellobiose and glucose. With cellotetraose as substrate, only cellobiose was formed. Thus the second glucosidic linkage was cleaved uniquely by the enzyme. Cellopentaose was largely converted into cellobiose, cellotriose, and some glucose, indicating that some cellotriose was further hydrolyzed to yield cellobiose and glucose. The hydrolysis patterns of cellooligosaccharides by CelF are very similar to those by CBHII from T. reesei [Harjunpää et al. (1996) Eur. J. Biochem. 240, 584–591].

Figure 3:
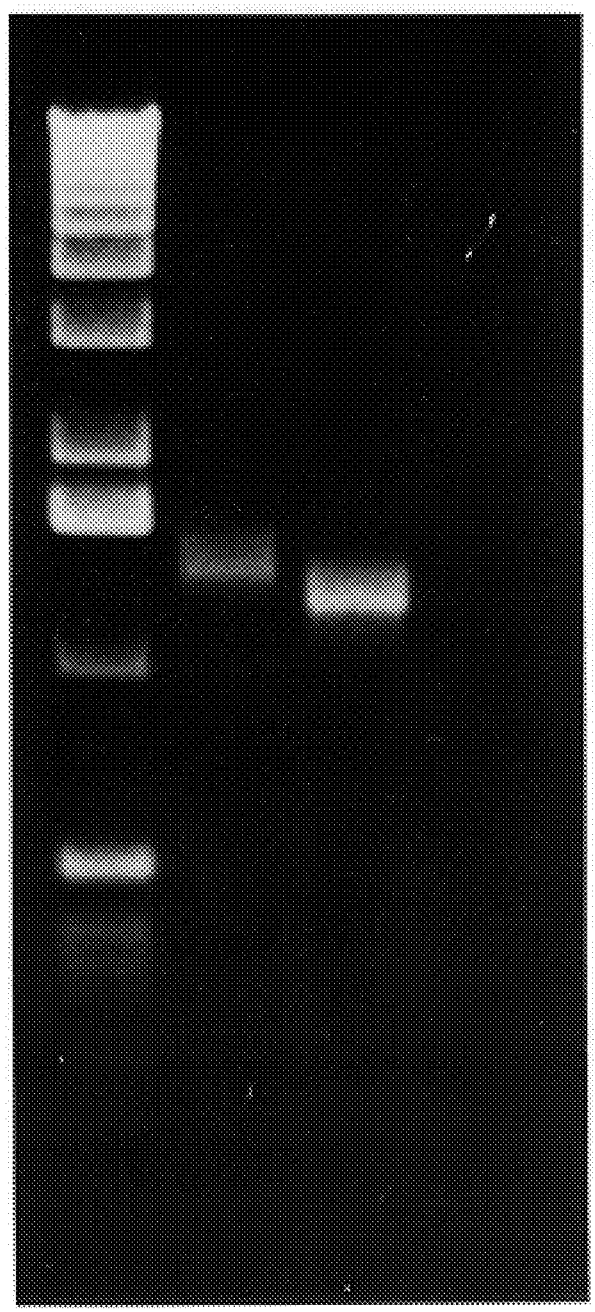
FIG. 3 shows the results of amplification of genomic DNA of Orpinomyces PC-2 celF coding region by PCR. Reaction solutions (20 μl) with genomic DNA (lane 1) and cDNA (lane 2) as the templates and without template (lane 3) were run on 1.5% agarose gel. DNA molecular standards were used in lane M. After electrophoresis, DNA bands were visualized by ethidium bromide staining.

The ORF region of celF genomic DNA was amplified by PCR, and its size is larger than that amplified from cDNA (FIG. 3). Sequencing the DNA amplified from the genomic DNA template after cloning it into pCRII revealed that it contained an 1,410 bp DNA insert. Alignment of the sequences of genomic and cDNA of celF revealed an intron (Table 3, SEQ ID NO:1) located in the N-terminal part of ORF with 111 bp occupying positions from 187 to 297. Splicing boundaries started with GT and ended with TA, which match the general consensus sequences found for introns in filamentous fungi [Gurr et al. (1987) In J. R. Kinghorn (ed.), p. 93–139. Gene structure in eukaryotic microbes, IRL Press, Oxford, UK]. In a similar experiment, the ORF regions of celA and celC genomic DNA were amplified by PCR and their sizes were the same as those amplified from their cDNAs, indicating that celA and celC are devoid of introns. Other genes coding for cellulolytic enzymes of anaerobic fungi, which have been examined, are devoid of introns [Chen et al. (1997) J. Bacteriol. 179, 6028–6034; Chen et al. (1998) FEMS Microbiol. Letts. 159, 63–68; Li et al. (1997) *Appl. Environ. Microbiol.* 63, 628–635; Liu et al. (1997) *Can. J. Microbiol.* 43, 477–485; Zhou et al. (1994) *Biochem. J.* 297, 359–364]. Since the intron of celF was located at CBD coding region corresponding to the NCRPD coding regions in celA and celC, no introns in celA and celC should be expected. The fact that the celF gene contains an intron within its ORF indicates that it has a fungal origin.

Using the software package PHYLIP (version 3.5) [Felsenstein, J. (1989) *Cladistics* 5, 164–166], a phylogenetic tree based on cellulase sequences was created from neighbor-joining bootstrap analysis. It showed that CelF, CelA, CelC, and *N. patriciarum* CelA were clustered together and their evolutionary positions were close to that of CBHIIs from aerobic fungi. It has been suggested that a common ancestral precursor of cellulolytic aerobic fungi and rumen anaerobic fungi may have existed [Denman et al. (1996) *Appl. Environ. Microbiol.* 62, 1889–1896]. The presence of an intron in celF provides evidence that CBHIIs in Orpinomyces PC-2 has a fungal origin. To date, two types of cellulases have been discovered in anaerobic fungi. One type includes endoglucanases possibly transferred from rumen bacteria [Chen et al. (1998) *FEMS Microbiol. Letts.* 159, 63–68; Gilbert et al. (1992) *Mol. Microbiol.* 6, 2065–2072; Li et al. (1997) *Appl. Environ. Microbiol.* 63, 628–635; Zhou et al. (1994) *Biochem. J.* 297, 359–364], the other is Orpinomyces CelA, CelC, CelF and Neocallimastix CELA which appear to have fungal origin [Denman et al. (1996) *Appl. Environ. Microbiol.* 62, 1889–1896; Li et al. (1997) *Appl. Environ. Microbiol.* 63, 4721–4728]. As discussed earlier, CelF having a CBD and lacking an NCRPD may not be part of a cellulosomal type complex of Orpinomyces PC-2. However, current observations seem to indicate that CelF has originated from aerobic fungi and that in these fungi an event may have occurred which led to a replacement of the CBD including its intron with an NCRPD. This event led to the formation of either CelA or CelC. The similarity of CelA and CelC [Li et al. (1997) *Appl. Environ. Microbiol.* 63, 4721–4728] indicates a gene duplication. These two enzymes having NCRPD are part of the cellulosomal complex, where CelF is not.

It will be understood by those skilled in the art that other nucleic acid sequences besides that disclosed herein for celF will function as coding sequences synonymous with the exemplified coding sequences. Nucleic acid sequences are synonymous if the amino acid sequences encoded by those nucleic acid sequences are the same. The degeneracy of the genetic code is well known to the art. For many amino acids, there is more than one nucleotide triplet which serves as the codon for a particular amino acid, and one of ordinary skill in the art understands nucleotide or codon substitutions which do not affect the amino acid(s) encoded. It is further understood in the art that codon substitutions to conform to common codon usage in a particular recombinant host cell is sometimes desirable.

Specifically included in this invention are sequences from other strains of Orpinomyces and from other anaerobic fungi which hybridize to the sequence disclosed for celF under stringent conditions. Stringent conditions refer to conditions understood in the art for a given probe length and nucleotide composition and capable of hybridizing under stringent conditions means annealing to a subject nucleotide sequence, or its complementary strand, under standard conditions (i.e., high temperature and/or low salt content) which tend to disfavor annealing of unrelated sequences, (indicating about 95–100% nucleotide sequence identity). Also specifically included in this invention are sequences from other strains of Orpinomyces and other anaerobic fungi which hybridize to the sequences disclosed for celF under moderately stringent conditions. Moderately stringent conditions refer to conditions understood in the art for a given probe sequence and "conditions of medium (moderate) stringency" means hybridization and wash conditions of 50°–65° C., 1× SSC and 0.1% SDS (indicating about 80–95% nucleotide sequence identity). Also specifically included in this invention are sequences from other strains of Orpinomyces from other anaerobic fungi, and from other organisms, including humans, which hybridize to the sequences disclosed for celF under highly stringent conditions. Highly stringent conditions refer to conditions understood in the art for a given probe sequence and "conditions of high stringency" means hybridization and wash conditions of 65°–68° C., 0.1× SSC and 0.1% SDS (indicating about 95–100% similarity). Hybridization assays and conditions are further described in Sambrook et al. (1989) supra.

A method for identifying other nucleic acids encoding celF-homologous enzymes is also provided, wherein nucleic acid molecules encoding cellulases are isolated from an anaerobic fungus, and nucleic acid hybridization is performed with the nucleic acid molecules and a labeled probe having a nucleotide sequence that includes all or part of nucleotide sequence SEQ ID NO: 1. By this method, silencing genes similar to the exemplified celF gene may be identified and isolated from other strains of Orpinomyces or other anaerobic fungi. All or part of a nucleotide sequence refers specifically to all continuous nucleotides of a nucleotide sequence, or e.g. 1000 continuous nucleotides, 500 continuous nucleotides, 100 continuous nucleotides, 25 continuous nucleotides, and 15 continuous nucleotides.

Sequences included in this invention are those amino acid sequences which are 75% similar to the amino acid sequences encoded by the exemplified Orpinomyces PC-2 CelF. Sequences included in this invention are also those amino acid sequences which are 80, 85, 90, 95 to 100%, and all integers between 75% and 100%, similar to the amino acid sequences encoded by exemplified Orpinomyces CelF.

It is well-known in the biological arts that certain amino acid substitutions may be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate, and isoleucine and valine, are both pairs of similar amino acids. Similarity between amino acid pairs has been assessed in the art in a number of ways. For example, Dayhoff et al. (1978) in Atlas of Protein Sequence and Structure, Volume 5, Supplement 3, Chapter 22, pp. 345–352, which is incorporated by reference herein provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Monoclonal or polyclonal antibodies, preferably monoclonal, specifically reacting with the particular cellulase enzyme (CelF) of the present invention may be made by methods known in the art. See, e.g., Harlow and Lane (1988) *Antibodies: A Laboratory Manual,* Cold Spring Harbor Laboratories; Goding (1986) *Monoclonal Antibodies: Principles and Practice,* 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, New York; Maniatis et al. (1982) *Molecular Cloning,* Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics,* Cold Spring Harbor Laboratory, Cold Spring Harbor, New York; Old and Primrose (1981) *Principles of Gene Manipulation, University of California Press, Berkeley;* Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; and Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein.

Each reference cited in the present application is incorporated by reference herein.

The following examples are provided for illustrative purposes, and is not intended to limit the scope of the invention as claimed herein. Any variations in the exemplified articles which occur to the skilled artisan are intended to fall within the scope of the present invention.

EXAMPLES

Example 1

Strains, Vectors, Construction, and Screening of an Orpinomyces CDNA Library.

Orpinomyces sp. strain PC-2 [Borneman et al. (1989) *Appl. Environ. Microbiol.* 55, 1066–1073] was grown as previously described [Chen et al. (1997) *J. Bacteriol.* 179, 6028–6034]. *Escherichia coli* XL1-Blue, λZAPII, and pBluescript SK(−) were purchased from Stratagene Cloning Systems (La Jolla, Calif.).

Extraction of RNA, purification of mRNA, and construction of a cDNA library for Orpinomyces PC-2 in λZAPII (Stratagene, La Jolla, Calif.) were described previously [Chen et al. (1995) *Proc. Natl. Acad. Sci. USA* 92, 2587–2591]. Isolation of cellulase-producing plaques was done as described previously [Chen et al. (1997) *J. Bacteriol.* 179, 6028–6034; Chen et al. (1998) *FEMS Microbiol. Letts.* 159, 63–68; Li et al. (1997) *Appl. Environ. Microbiol.* 63, 4721–4728], with carboxymethylcellulose (CMC) as the substrate. Top agar containing 5 mM isopropyl-β-D-thiogalactoside to induce recombinant gene expression via lac promoter sequences and 0.2% remazol brilliant blue (RRB)-carboxymethyl cellulose (CMC) (InterSpex Products, Inc., Foster city, Calif.) or RBB-xylan (Sigma Chemical Co., St. Louis, Mo.) was used to identify cellulose- and xylanase-producing clones. Positive clones were identified by their clear haloes on a blue background due to diffusion of RBB after hydrolysis of RBB-CMC or RBB-xylan. Pure clones were obtained after a secondary screening. λZAPII phages were converted into pBluescript SK(−) derivatives by in vivo excision according to the manufacturer's instructions (Stratagene). pBluescript DNAs were purified from cultures grown overnight in Luria-Bertani (LB)-ampicillin (50 μg/ml) medium using a spin column miniprep kit (Qiagen, Chatsworth, Calif.). Nucleotide sequences of insert DNA were determined with an automatic DNA sequencer (Applied Biosystems, Foster City, Calif.). Both universal and specific primers were used to sequence both strands of the inserts. Sequence data were analyzed using the Genetic Computer Group (GCG) version 8 (University of Wisconsin Biotechnology Center, Madison, Wis.) on the VAX/VMS system of the BioScience Computing Resource at the University of Georgia.

Example 2

Enzyme Preparation.

A single colony of *E. coli* XL-1 Blue harboring pCEL8 grown on LB-ampicillin plate was inoculated into a flask containing 500 ml of LB-ampicillin liquid medium containing ampicillin at a concentration of 50 μg/ml. The culture was shaken (280 rpm) at 37° C. and grown to an $OD_{600}$ of approximately 1.0. Isopropyl-1-thio-β-D-galactopyranoside (1 mM) was added to induce celF expression, and the culture was incubated for another 4 h. Cells were harvested by centrifugation (5,000× g, 10 min), washed with 50 ml of buffer containing 50 mM sodium citrate (pH 6.0) and resuspended in 30 ml of the same buffer. The cells were then disrupted by sonication (four times at 7,000 cycles in a Branson Sonifier 450, Danbury, Conn.). Cell debris was removed by centrifugation (15,000× g, 10 min). The supernatant fraction was used for enzyme assays.

Example 3

Zymogram Analysis.

Enzyme samples were pretreated by incubating for 1 h at 40° C. in SDS-PAGE sample buffer, and SDS-PAGE was carried out in 10% to 20% gradient polyacrylamide gels at 4° C. [Laemmli, U.K. (1970) *Nature* 227, 680–685]. To enhance removal of SDS and recovery of enzymatic activity following SDS-PAGE, gels were pre-washed in 50 mM sodium citrate buffer, pH 6.0 with 1% (w/v) bovine serum albumin (BSA). Enzyme activities were detected using the zymogram method of Béguin [Béguin, P. (1983) *Anal. Biochem.* 131, 333–336] with a overlay containing lichenin (0.2%, w/v) and agarose (2%, w/v) in the same buffer.

Example 4

Enzyme Assays and Analytical Methods.

All enzyme assays were carried out in duplicate in 50 mM sodium citrate buffer at pH 6.0 and 40° C. unless otherwise stated. Carboxymethyl cellulase (CMCase) activity was assayed by mixing a 0.2 ml aliquot of appropriately diluted enzyme with 0.4 ml buffer containing 1% (w/v) CMC. The reaction mixture was incubated for 30 min, and it was terminated by the addition 1.2 ml of 31 mM dinitrosalicylic acid (DNS) reagent [Miller, G. L. (1959) Anal. Chem. 31, 426–428]. Glucose was used as standard. Reducing sugars were measured by reading the absorbance at 550 nm. The hydrolysis of other polysaccharides was tested in a manner similar to that for CMC. Activity measurements of enzyme preparations towards p-nitrophenol (pNP) linked substrates were performed in 0.3 ml buffer containing 2 mM substrates. Reactions were terminated after 10 min by addition of 0.8 ml 1 M $Na_2CO_3$. The release of pNP was measured by reading the absorbance at 405 nm. pNP was used as standard. One unit (U) of enzyme activity was defined as the amount of enzyme required to release one μmol glucose equivalent per min. Specific activity, was expressed as units per mg of protein. Protein concentration was determined by the Bradford method [Bradford, M. M. (1976) Anal. Biochem. 72, 248–254] and the Coomassie protein assay reagent from Pierce Chemical Co. in duplicate sets using BSA as standard.

Sugars released from cellooligosaccharides were analyzed with a Hewlett-Packard 1100 series HPLC equipped with an autoinjector and a 1047A RI detector using a Bio-Rad Aminex HPX-42A carbohydrate column. Water was used as the mobile phase at a flow rate of 0.6 ml/min and the column temperature was set at 80° C. Reaction mixtures contained 0.25 U/ml enzyme with 3 mM of cellooligosaccharides. Glucose, cellobiose, cellotriose, cellotetraose and cellopentaose were used as standards.

Example 5
Adsorption Assay.

For assays of cellulose binding capability, enzyme samples of 1 mg were mixed with 30 mg Avicel in a final volume of 1 ml of buffer (50 mM sodium citrate buffer at pH 6.0) at 4° C. After 1 h with continuous shaking, the Avicel was removed by centrifugation (15,000× g, 4° C.). Unbound enzyme left in the supernatant was determined and the amount of enzyme bound to the Avicel was the difference between this value and that before the Avicel adsorption.

Example 6
Analysis of genomic DNA.

Oligonucleotides 5'ATGAAAATTTTACTTTTTGC-CAG3' (SEQ ID NO:3) and 5'TTAGAATCCTGGTCTAG-CATTTC3' (SEQ ID NO:4) corresponding to opposite strands of the end regions of celF open reading frame (ORF) (see FIG. 1) were used as primers with genomic DNA [Chen et al. (1997) J. Bacteriol. 179, 6028–6034] and the cDNA library as templates for polymerase chain reactions (PCR), which were performed on a 480 Thermal Cycler (Perkin-Elmer Co., Norwalk, Conn.). Amplification was for 30 cycles with each cycle consisting of 90 s of melting at 95° C., 60 s of annealing at 55° C., and 90 s of extension at 72° C. Reaction solutions (20 μl) were separated on a 1.5% (w/v) agarose, and DNA bands were visualized by ethidium bromide staining. The PCR products amplified from the genomic DNA were cloned into PCRII vector (Invitrogen, Carlsbad, Calif.) and sequenced as described above.

The GenBank accession numbers for the cDNA and genomic DNA sequences of celF are U97154 and AF031934, respectively.

TABLE 1

Substrate specificity of CelF produced in E. coli[a]

| Substrate[b] | Specific activity (U/mg protein) |
|---|---|
| Avicel | 0.09 |
| Amorphous-swollen cellulose | 1.8 |
| CMC | 2.6 |
| Barley β-glucan | 21.7 |
| Lichenin | 15.7 |

[a]Assays were performed at 40° C. and pH 6.0 (50 mM sodium citrate) for 10 min (pNP-β-glycosides), 15 min (oat spelt xylan, barley β-glucan and lichenin), 30 min (CMC), and 4 h (Avicel), respectively.
[b]The activities with pNP-β-D-glucoside, pNP-β-D-cellobioside, oat spelt xylan, or pNP-β-D-xyloside as substrate were less than 1.0% of that of CMC.

TABLE 2

HPLC analysis of products of cellooligosaccharides by CelF produced in E. coli[a]

| | Products or residual substrates (μmol/ml) | | | |
|---|---|---|---|---|
| Substrate | G1 | G2 | G3 | G4 |
| Cellotriose (G3) | 0.3 | 0.2 | 2.7 | — |
| Cellotetraose (G4) | — | 5.8 | — | — |
| Cellopentaose (G5) | 0.2 | 3.3 | 2.7 | — |

[a]Reaction mixtures contained 0.25 U/ml enzyme (CMC as substrate) and 3 mM of cellooligosaccharides in 20 mM sodium citrate. Reactions were at pH 6.0 and 40° C. and for 4 h.

TABLE 3

Genomic DNA and deduced amino acid sequences celF from *Orpinomyces* sp. strain PC-2. A typical fungal cellulose binding domain (CBD) is underlined. An extremely Asn-rich linker is double underlined. The intron is indicated by small letters. The asterisk indicates the stop codon.

| | |
|---|---|
| AAAAATTAAATTTTGTAATATTTTTTATTTGATATAAAAAAAATATTAGTAAATTTTT | 60 |
| ATAAACCTTTTTCTAATTATTTAAAAAAAGCACAATGAAAATTTTACTTTTTGCCAGTAT | 120 |
|                                                           M  K  I  L  L  F  A  S  I | 9 |
| TCTTAGTTTTGGTCTTGTAAATTTTGCTAACGCTGCTTGTGGTGGTGCTTATGCTCAATG | 180 |
| L  S  F  G  L  V  N  F  A  N  A  A  <u>C  G  G  A  Y  A  O  C</u> | 29 |
| TGGAGGgtatggatattttattttaaatttaggaaataaatactttaaataatttaa | 240 |
| <u>G  G</u> | 31 |

TABLE 3-continued

Genomic DNA and deduced amino acid sequences celF from *Orpinomyces* sp. strain PC-2. A typical fungal cellulose binding domain (CBD) is underlined. An extremely Asn-rich linker is double underlined. The intron is indicated by small letters. The asterisk indicates the stop codon.

| | | |
|---|---|---|
| tttaagtattgattattttaaattattatattacttataacaaattaagatatatagTGA | | 300 |
| | E | 32 |
| AAACTTTTACGGTGAAAAATGTTGTGTTTCTGGTTACAAATGTGTTTATATGAATCAATG | | 360 |
| <u>NFYGEKCCVSGYKCVYMNOW</u> | | 52 |
| GTATTCTCAATGTCAACCAGGTGCTTCATCATCAAATCCACCTTCTAATAATGCTTCTAA | | 420 |
| <u>YSOCO</u> P G A S S S N P P <u>SNNASN</u> | | 72 |
| CAATAATAACAATGATAACAACAACAACAACAACAATAATAATAATAATAATAATAATAA | | 480 |
| <u>NNNNDNNNNNNNNNNNNNNN</u> | | 92 |
| TAATAATAATAATAATAACTCTGGTAGTGGAAGTACTCAAAACTTCTTCACTAATCAAAT | | 540 |
| <u>NNNNNNSGSGSTO</u> N F F T N Q I | | 112 |
| TTATGCTAATCCAAAATTCATTGAAGAAGTCAATTCTTCTATTCCAAAATTAAGTTGGGA | | 600 |
| Y A N P K F I E E V N S S I P K L S W D | | 132 |
| CTTACAACAAAAGGCTCAAAAGGTTAAGGATGTTCCAACTGCTGTTTGGTTAGCTTGGGA | | 660 |
| L Q Q K A Q K V K D V P T A V W L A W E | | 152 |
| AGGTGCTCCAGGTGAAGTTGAACAACATCTTAAGGCTGCTGGTTCTAAAACTGTTGTATT | | 720 |
| G A P G E V E Q H L K A A G S K T V V F | | 172 |
| TATTCTTTACATGATTCCAACTCGTGATTGTAATAGTAATGCTTCTGCTGGTGGTGCCGG | | 780 |
| I L Y M I P T R D C N S N A S A G G A G | | 192 |
| TAGTCTTAACACTTACAAGGGTTATGTTGACAACATTTCTAGAACTATTCGTAGTTATCC | | 840 |
| S L N T Y K G Y V D N I S R T I R S Y P | | 212 |
| AAACTCTAAGGTTGTTATGGTTCTTGAACCAGATACTCTTGGTAATCTTGTTACTGGTAA | | 900 |
| N S K V V M V L E P D T L G N L V T G N | | 232 |
| CAGTGCTAACTGTCAAAACGTCCGTCAATTACACAAGAACGCTTTATCCTATGCTGTTAA | | 960 |
| S A N C Q N V R Q L H K N A L S Y A V N | | 252 |
| TGTTTACGGTGCTATGAATAATGTTAGTGTTTACCTTGATGCTGCCCATGGTAAATGGTT | | 1020 |
| V Y G A M N N V S V Y L D A A H G K W L | | 272 |
| AGGTGGTGTTACTGATAAGGTTGCTGCTGTTGTTAAGGAAATCTTAAACAATGCTCCAAA | | 1080 |
| G G V T D K V A A V V K E I L N N A P N | | 292 |
| TGGTAAAATTCGTGGTTTAAGTACTAACGTTTCTAACTACCAACCAATTGCTTCTGAATA | | 1140 |
| G K I R G L S T N V S N Y Q P I A S E Y | | 312 |
| CTCCTACCACCAAAAGCTTGCTTCCTCTCTTTCTGCTGTTGGTATTCCAAACATGCACTT | | 1200 |
| S Y H Q K L A S S L S A V G I P N M H F | | 332 |
| TATTGTTGATACTGGCCGTAATGGTGTTGATGTTAGTGCTGCTTTCAATACATCTGAAAC | | 1260 |
| I V D T G R N G V D V S A A F N T S E T | | 352 |
| TTGGTGTAACTTTGTAGGTACTGGTTTTGGTGAACGTCCAAGAGGTAATCCAAACTCAGG | | 1320 |
| W C N F V G T G F G E R P R G N P N S G | | 372 |
| TATGCCATTATTAGATGCTTACATGTGGCTTAAGACTCCACGAGAATCTGATGGTTCTTC | | 1380 |
| M P L L D A Y M W L K T P R E S D G S S | | 392 |
| CTCTGGTAGTAGAGCTGATCCAGTTTGTTCTCGTTCTGATTCTCTTAGAGGTGCACCAGA | | 1440 |
| S G S R A D P V C S R S D S L R G A P D | | 412 |
| CGCAGGTCAATGGTTCCACGATTATTTCGTTCAATTATTAAGAAATGCTAGACCAGGATT | | 1500 |
| A G Q W F H D Y F V Q L L R N A R P G F | | 432 |
| CTAAGTTAATTAAGAAGAAAAAAAAAGATGATAAAAAAATTTCAGTATTAATTATTCTTT | | 1560 |
| * | | |
| TTACTATTACTAATTAAATGAATAATAGATAAAATATATACTATATATCATTTATTGATG | | 1620 |
| ATATAAAGTTT | | 1631 |

We claim:

1. A non-naturally occurring recombinant DNA molecule comprising a first nucleotide sequence encoding a mature CelF cellulase, wherein said first nucleotide sequence being nucleotides 158 to 186 of SEQ ID NO:1 joined to nucleotides 298 to 1501 of SEQ ID NO:1, excluding a translation stop codon, or a second nucleotide sequence encoding a mature CelF cellulase, wherein said second sequence hybridizes to said first sequence under DNA:DNA hybridization conditions of moderate stringency, wherein the conditions of moderate stringency include hybridization and wash conditions of 50–60° C., 1× SSC and 0.1% sodium SDS, and wherein said CelF cellulase has characteristics of an endoglucanase or cellobiohydrolase having hydrolytic activity for carboxymethylcellulose, barley β-glucan, lichenin and para-nitrophenyl-β-D-cellobioside.

2. The non-naturally occurring recombinant DNA molecule of claim 1 wherein said nucleotide sequence encodes a mature cellulase having an amino acid sequence as given in SEQ ID NO:2, amino acids 22 to 432.

3. The non-naturally occurring recombinant DNA molecule of claim 1 wherein said nucleotide sequence encoding said mature cellulase is as given in SEQ ID NO:1, nucleotides 158–186, joined to nucleotides 298 to 1501, exclusive of a transcription termination codon.

4. The non-naturally occurring recombinant DNA molecule of claim 1 wherein the nucleotide sequence encoding the mature cellulase further comprises a second nucleotide sequence encoding a signal peptide operably linked 5' to the first nucleotide sequence.

5. The non-naturally occurring recombinant DNA molecule of claim 4 wherein the second nucleotide sequence encodes a signal peptide having an amino acid sequence as given in SEQ ID NO:2, amino acids 1 to 21.

6. The non-naturally occurring recombinant DNA molecule of claim 5 wherein the second nucleotide sequence encoding the signal peptide is as given in SEQ ID NO:1, nucleotides 95 to 157.

7. The DNA molecule of claim 1 wherein between the joined sequences is a sequence as given in SEQ ID NO:1, nucleotides 187 to 297.

8. A recombinant host cell comprising the non-naturally occurring recombinant DNA molecule of claim 1.

9. The recombinant host cell of claim 8 wherein the nucleotide sequence encodes a mature cellulase having an amino acid sequence as given in SEQ ID NO:2, amino acids 22 to 432.

10. The recombinant host cell of claim 9 wherein said nucleotide sequence encoding said mature cellulase is as given in SEQ ID NO:1, nucleotides 158 to 186, joined to nucleotides 298 to 1501, exclusive of a translation termination codon.

11. The recombinant host cell of claim 10 wherein the nucleotide sequence encoding the mature cellulase further comprises a second nucleotide sequence encoding a signal peptide operably linked 5' to the first nucleotide sequence.

12. The recombinant host cell of claim 11 wherein the second nucleotide sequence encodes a signal peptide having an amino acid sequence as given in SEQ ID NO:2, amino acids, 1 to 21.

13. The recombinant host cell of claim 12 wherein the second nucleotide sequence encoding the signal peptide is as given in SEQ ID NO:1, nucleotides 95 to 157.

14. The recombinant host cell of claim 9, wherein between the joined sequences is a sequence as given in SEQ ID NO:1, nucleotides 187 to 297.

15. A method of producing recombinant cellulase in a recombinant host cell, said method comprising the steps of:

(a) transforming or transfecting a host cell to contain and express a non-naturally occurring recombinant DNA molecule comprising a first nucleotide sequence encoding a mature CelF cellulase, wherein said first nucleotide sequence is as given in SEQ ID NO:1, nucleotides 158 to 186, and further including, immediately 3' thereto, nucleotides 298 to 1501, excluding a translation stop codon, or a second nucleotide sequence encoding a mature CelF cellulase, wherein said second sequence hybridizes to said first sequence under DNA:DNA hybridization conditions of moderate stringency, wherein the conditions of moderate stringency include hybridization and wash conditions of 50–60° C., 1× SSC and 0.1% sodium SDS, and wherein said CelF cellulase has characteristics of an endoglucanase or cellobiohydrolase having hydrolytic activity for carboxymethylcellulose, barley β-glucan, lichenin and para-nitrophenyl-β-D-cellobioside; and (b) culturing the recombinant host cell of step (a) under conditions for expression of the cellulase.

16. The method of claim 15 wherein said nucleotide sequence encodes a mature cellulase having an amino acid sequence as given in SEQ ID NO:2, amino acids 22 to 432.

17. The method of claim 16 wherein said nucleotide sequence encoding said mature cellulase is as given in SEQ ID NO:1, nucleotides 158–186, joined to nucleotides 298 to 1501, exclusive of a transcription termination codon.

18. The method of claim 15 wherein the nucleotide sequence encoding the mature cellulase further comprises a second nucleotide sequence encoding a signal peptide operably linked 5' to the first nucleotide sequence.

19. The method of claim 18 wherein the second nucleotide sequence encodes a signal peptide having an amino acid sequence as given in SEQ ID NO:2, amino acids 1 to 21.

20. The method of claim 19 wherein the second nucleotide sequence encoding the signal peptide is as given in SEQ ID NO:1, nucleotides 95 to 157.

* * * * *

UNITED STATES PATENT AND TRADEMARK OFFICE
CERTIFICATE OF CORRECTION

PATENT NO. : 6,114,158
DATED : September 5, 2000
INVENTOR(S) : Li et al.

It is certified that error appears in the above-identified patent and that said Letters Patent is hereby corrected as shown below:

Title page,
Item [56], References Cited, OTHER PUBLICATIONS,
Line 2, in the Denman et al. reference, delete "CDNA" and replace with -- cDNA --.
Line 2, in the Gilkes et al. reference, delete "Conservatin" and replace with
-- Conservation --.
Line 2, in the second Li et al. reference, delete "Pc-2" and replace with -- PC-2 --.
Next to last line, in the Pages et al. reference, delete the space in "Do kerin" and replace with -- Dockerin --.
Line 2, in the Wilson reference, delete "isolatiion" and replace with -- isolation --.

Column 2,
Line 59, delete "10".

Column 12,
Line 6, delete "RRB" and replace with -- RBB --.

Column 14,
Line 2, delete "FIG.1" and replace with -- Figs. 1A and 1B --.

Column 33, claim 1,
Line 26, delete "sodium".

Column 33, claim 3,
Line 41, delete "transcription" and replace with -- translation --.

Column 34, claim 15(a),
Line 57, delete "sodium".

UNITED STATES PATENT AND TRADEMARK OFFICE
CERTIFICATE OF CORRECTION

PATENT NO. : 6,114,158
DATED : September 5, 2000
INVENTOR(S) : Li et al.

It is certified that error appears in the above-identified patent and that said Letters Patent is hereby corrected as shown below:

Column 35, claim 17,
Line 4, delete "transcription" and replace with -- translation --.

Signed and Sealed this

Fifth Day of March, 2002

Attest:

JAMES E. ROGAN
Attesting Officer     Director of the United States Patent and Trademark Office

UNITED STATES PATENT AND TRADEMARK OFFICE
CERTIFICATE OF CORRECTION

PATENT NO.   : 6,114,158
DATED        : September 5, 2000
INVENTOR(S)  : Li et al.

It is certified that error appears in the above-identified patent and that said Letters Patent is hereby corrected as shown below:

Column 2,
Line 65, delete "NO:1" and replace with -- NO:2 --.

Column 33,
Line 26, delete "sodium".
Line 41, delete "transcription" and replae with -- translation --.

Column 34,
Line 57, "a", delete "sodium".

Column 35,
Line 4, delete "transcription" and replace with -- translation --.

Signed and Sealed this

Twenty-eighth Day of January, 2003

JAMES E. ROGAN
*Director of the United States Patent and Trademark Office*